(12) United States Patent
Sobral et al.

(10) Patent No.: US 10,543,298 B2
(45) Date of Patent: Jan. 28, 2020

(54) SALTS OF TETRACYCLINES

(71) Applicant: Hovione Scientia Limited, Cork (IE)

(72) Inventors: Luis Sobral, Loures (PT); Livia Santana De Arruda, Rio de Janeiro (BR); Margarida Figueiredo, Pinhal Novo (PT); Rafael Antunes, Setubal (PT); Ana Paula Filipe, Loures (PT)

(73) Assignee: Hovione Scientia Limited, Cork (IE)

( * ) Notice: Subject to any disclaimer, the term of this patent is extended or adjusted under 35 U.S.C. 154(b) by 0 days.

(21) Appl. No.: 15/778,132

(22) PCT Filed: Nov. 24, 2016

(86) PCT No.: PCT/GB2016/053695
§ 371 (c)(1),
(2) Date: May 22, 2018

(87) PCT Pub. No.: WO2017/089809
PCT Pub. Date: Jun. 1, 2017

(65) Prior Publication Data
US 2018/0344903 A1 Dec. 6, 2018

(30) Foreign Application Priority Data

Nov. 24, 2015 (PT) .......................... 108978

(51) Int. Cl.
| | | |
|---|---|---|
| *A61L 29/16* | (2006.01) | |
| *C07C 231/12* | (2006.01) | |
| *C07C 237/26* | (2006.01) | |
| *A61L 31/16* | (2006.01) | |
| *A61K 31/65* | (2006.01) | |

(52) U.S. Cl.
CPC .............. *A61L 29/16* (2013.01); *A61L 31/16* (2013.01); *C07C 231/12* (2013.01); *C07C 237/26* (2013.01); *A61K 31/65* (2013.01); *A61L 2300/406* (2013.01); *A61L 2300/41* (2013.01)

(58) Field of Classification Search
CPC ................................ A61L 29/16; A61K 31/65
USPC ....................................................... 514/152
See application file for complete search history.

(56) References Cited

U.S. PATENT DOCUMENTS

| | | | |
|---|---|---|---|
| 2,878,289 | A | 3/1959 | McCormick et al. |
| 2,886,595 | A | 5/1959 | Heinemann et al. |
| 2,929,837 | A | 3/1960 | Ogawa et al. |
| 3,019,260 | A | 1/1962 | McCormick et al. |
| 3,042,716 | A | 7/1962 | Blackwood et al. |
| 3,200,149 | A | 8/1965 | Blackwood et al. |
| 3,226,436 | A | 12/1965 | Petisi et al. |
| 3,932,490 | A | 1/1976 | Fernandez |
| 4,877,559 | A | 10/1989 | Page et al. |
| 6,143,161 | A | 11/2000 | Heggie et al. |
| 2009/0099376 | A1 | 4/2009 | Bernatchez et al. |
| 2012/0064372 | A1 | 3/2012 | Raad |

FOREIGN PATENT DOCUMENTS

| | | | |
|---|---|---|---|
| BE | 615425 | A | 7/1962 |
| BE | 896423 | A | 8/1983 |
| CN | 103860474 | A * | 6/2014 |
| DE | 1045398 | B | 12/1958 |
| DE | 1593015 | A1 | 4/1970 |
| FR | 92088 | E | 9/1968 |
| GB | 901209 | A | 7/1962 |
| GB | 1228629 | A | 4/1971 |
| PT | 108978 | | 11/2015 |
| WO | 2010046932 | A2 | 4/2010 |
| WO | 2017089809 | A1 | 6/2017 |

OTHER PUBLICATIONS

English Translation of CN 103860474 A (2014).*
Foreign communication from a related application—Search Report of Portuguese Patent Application No. 108978, dated Sep. 6, 2016, in Portuguese language, 2 pages.
Carlborg, Björn, et al., "Tetracycline induced esophageal ulcers. A clinical and experimental study," The Laryngoscope, vol. 93, No. 2, Feb. 1983, pp. 184-187.
Corleto, Vito D., et al., "A case of oesophageal ulcer developed after taking homeopathic pill in a young woman," World Journal of Gastroenterology, vol. 13, No. 14, Apr. 14, 2007, pp. 2132-2134, The WJG Press.
Foreign Communication from a related application—International Search Report and Written Opinion of International Application No. PCT/GB2016/053695 dated Feb. 8, 2017, 11 pages.

(Continued)

*Primary Examiner* — Kevin E Weddington
(74) *Attorney, Agent, or Firm* — Conley Rose, P.C.; Rodney B. Carroll

(57) ABSTRACT

A tetracycline salt comprising a tetracycline and an organic acid wherein the organic acid is oxalic acid or maleic acid is provided. The tetracycline is preferably doxycycline, minocycline, sancycline, lymecycline, tetracycline or demeclocycline, and preferred salts include oxycycline maleate, minocycline oxalate, tetracycline oxalate, demeclocycline maleate, demeclocycline oxalate, sancycline maleate, lymecycline maleate, or lymecycline oxalate. A pharmaceutical formulation comprising a tetracycline salt according to the invention is also provided, as is a medical device having coated thereon a salt or pharmaceutical formulation according to the invention. A salt of the invention, or a formulation of the invention are also provided for use as medicaments, particularly for use in the treatment or prevention of an inflammation and/or an infection. There is also provided a method of preparing a tetracycline salt, which method comprises reacting a tetracycline base with an excess of an organic acid in a solvent.

23 Claims, 29 Drawing Sheets

(56) References Cited

OTHER PUBLICATIONS

Figure 1:
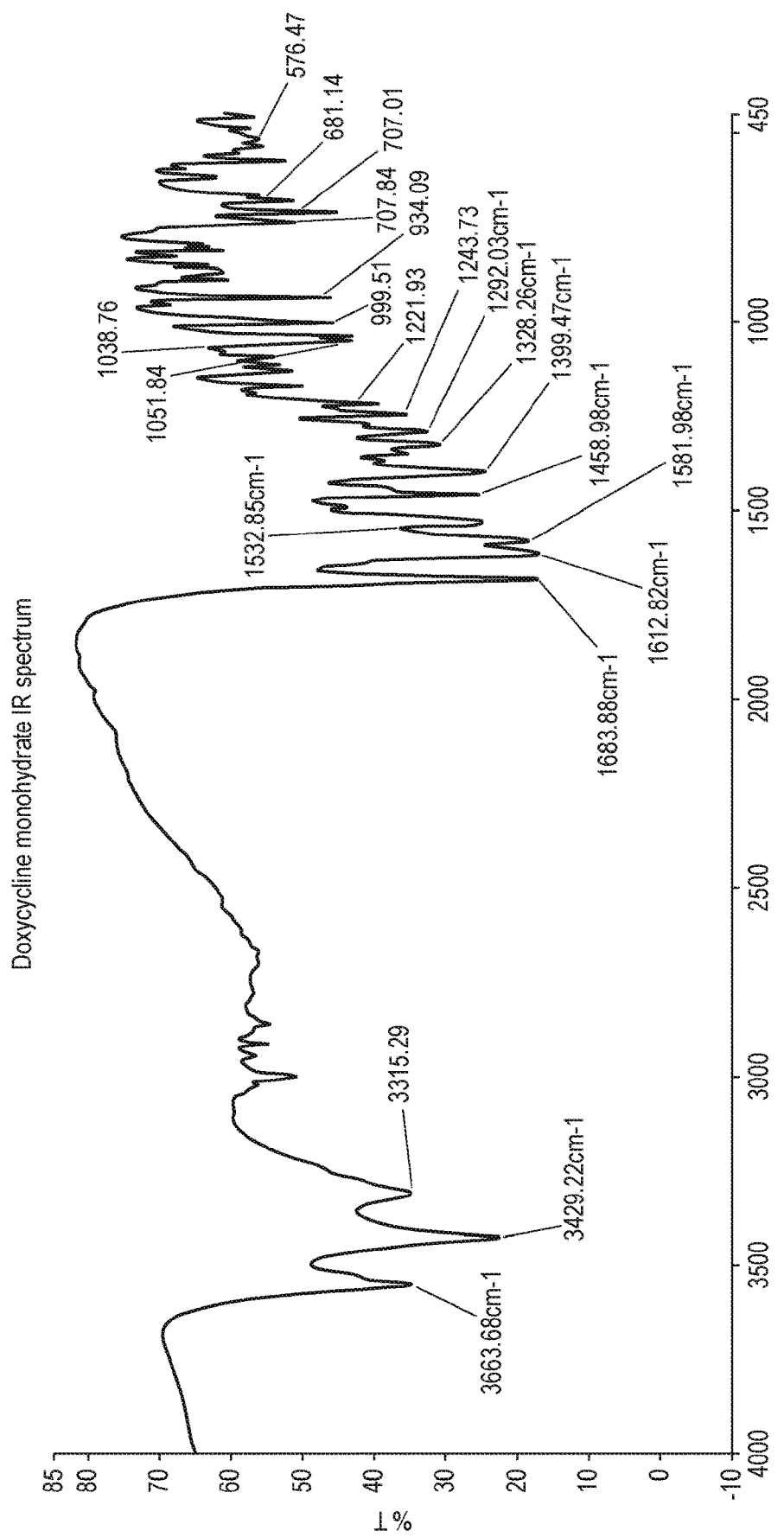
Figure 2:
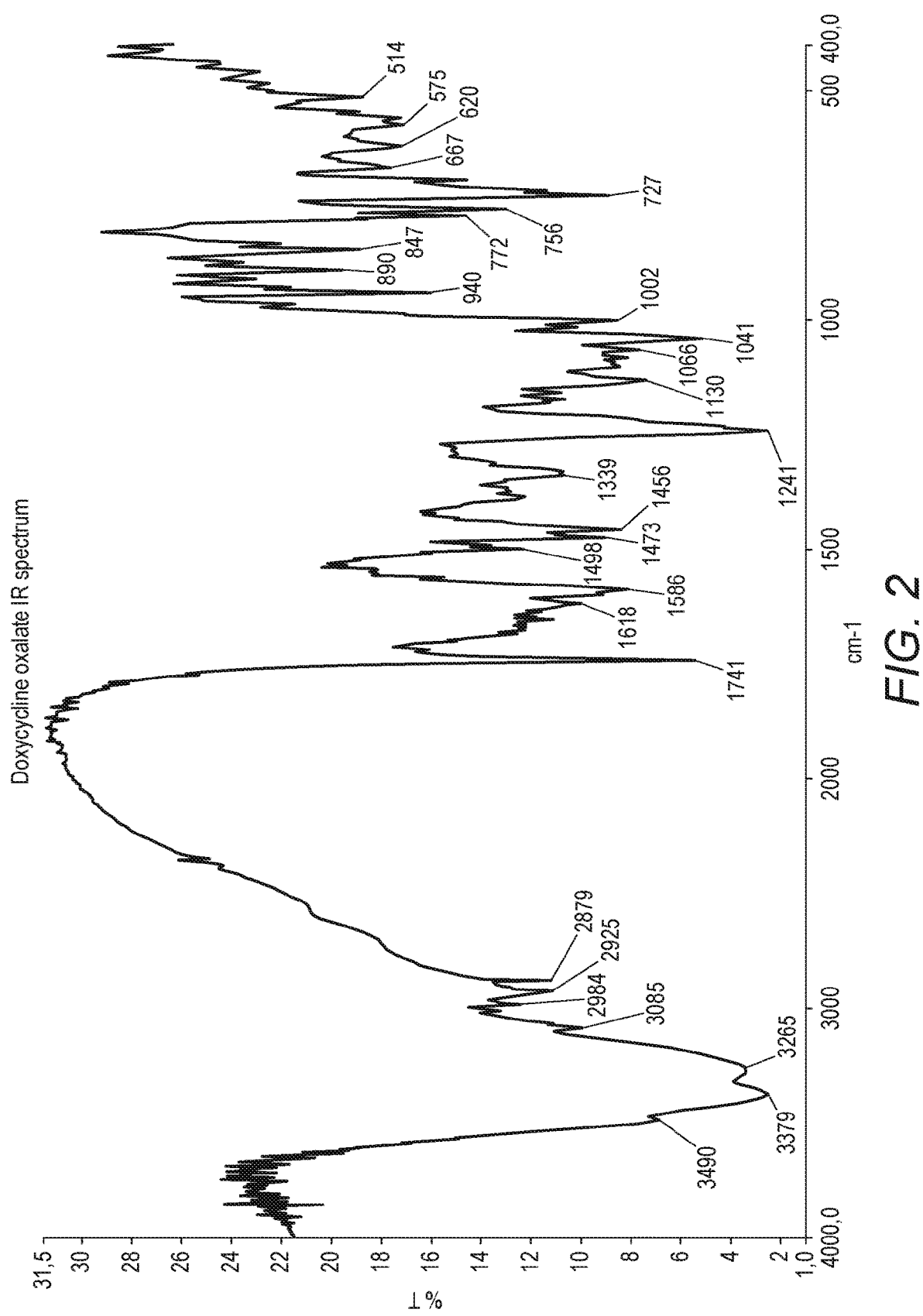
Figure 3:
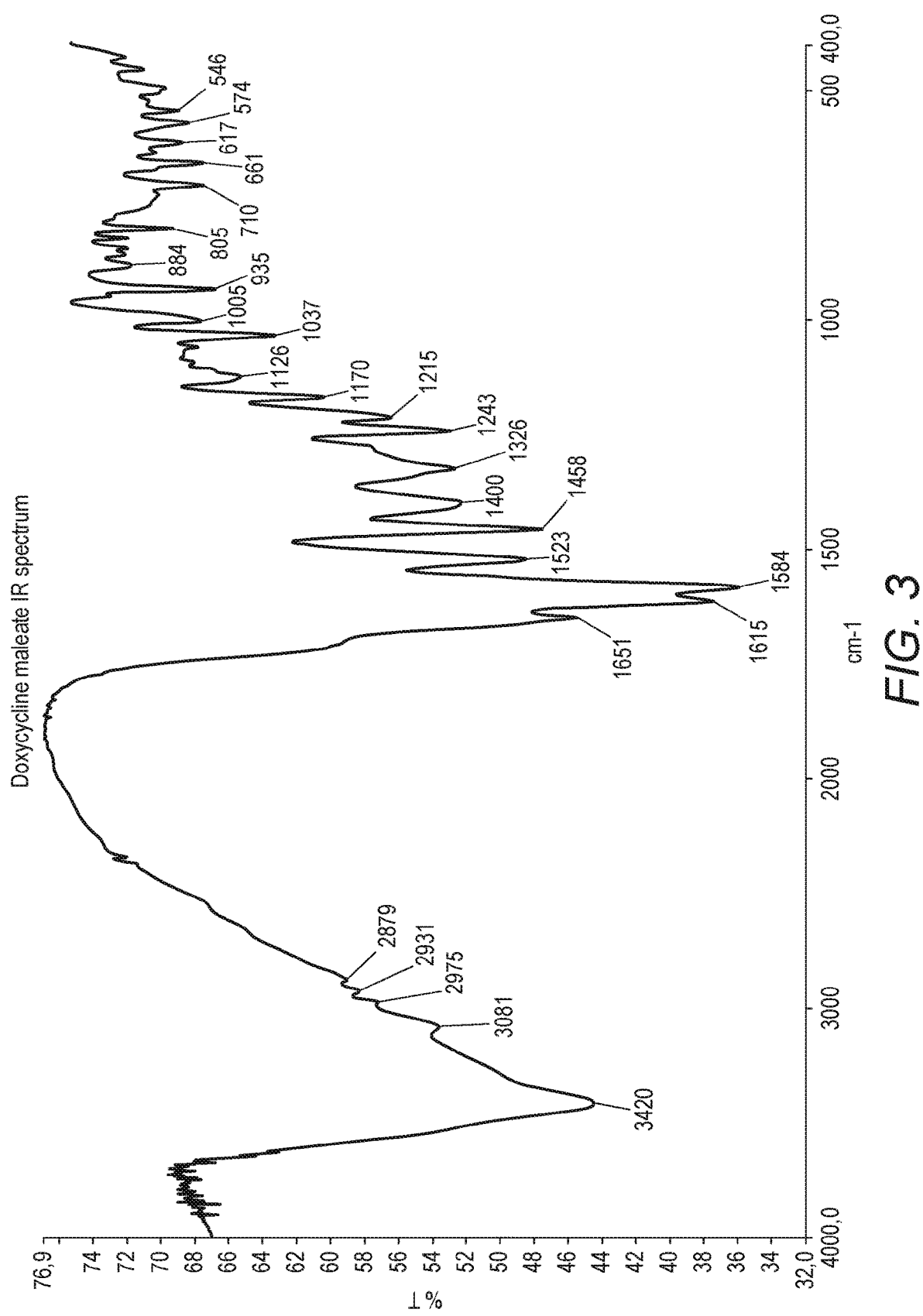
Figure 4:
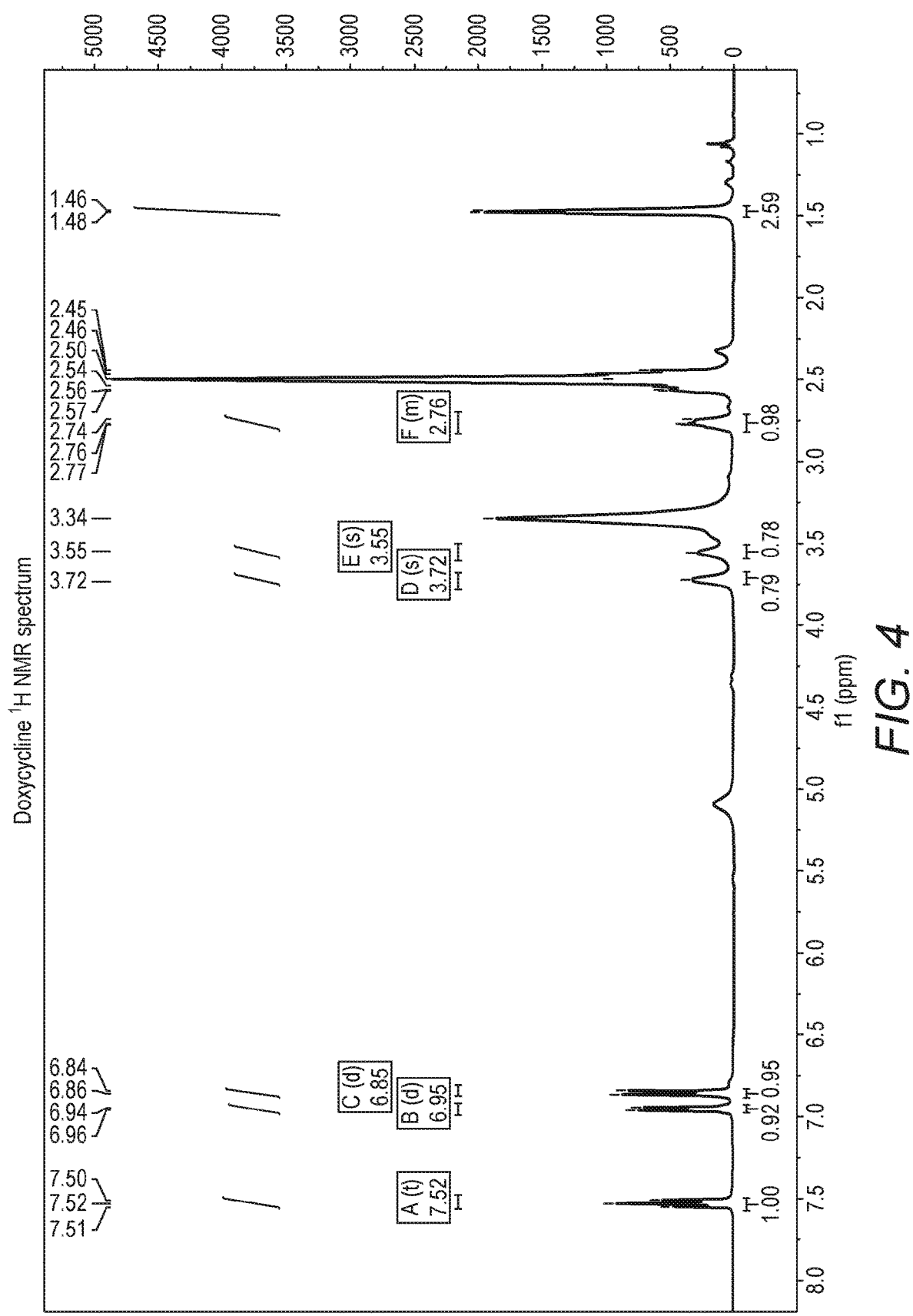
Figure 5:
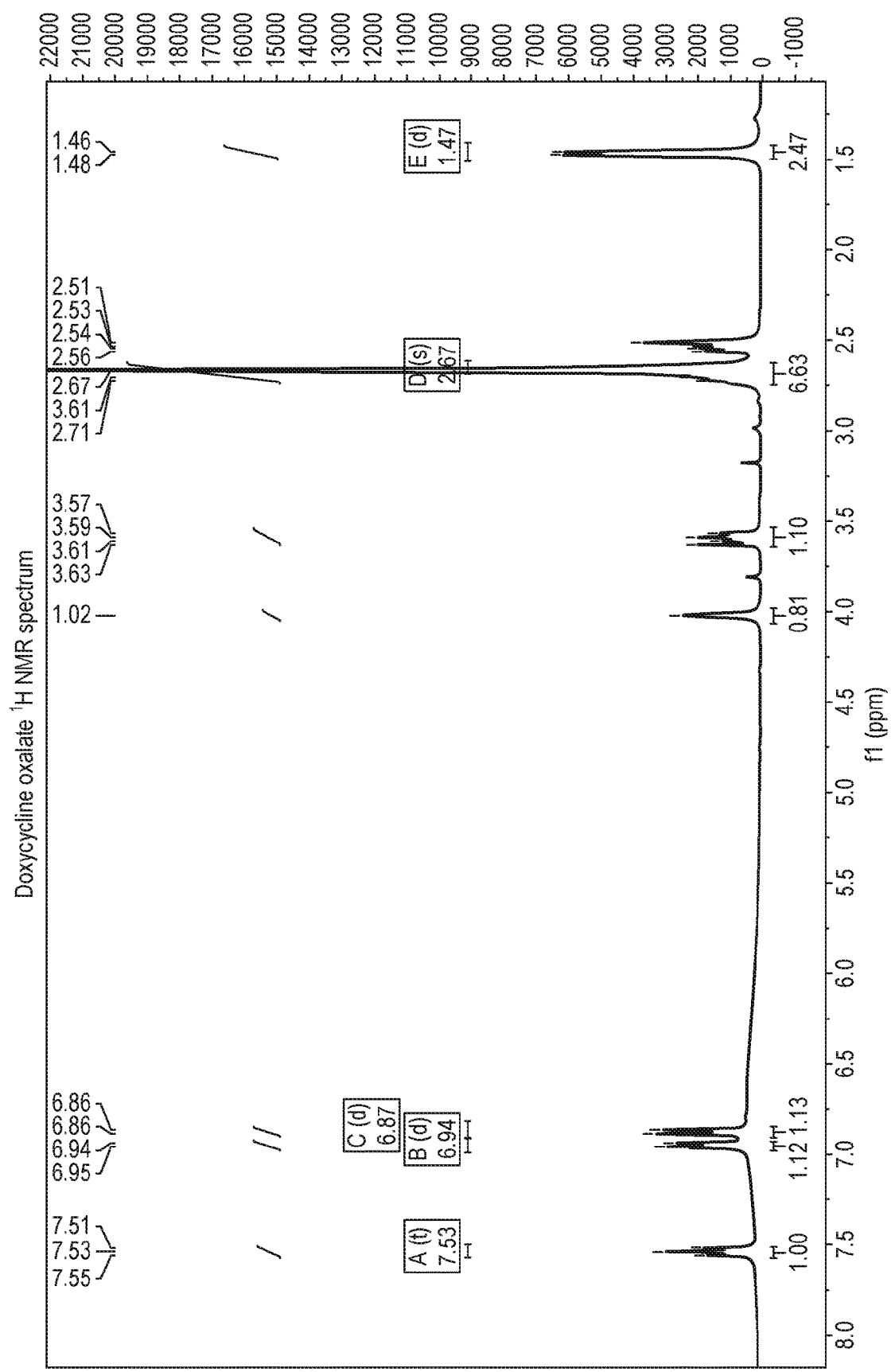
Figure 6:
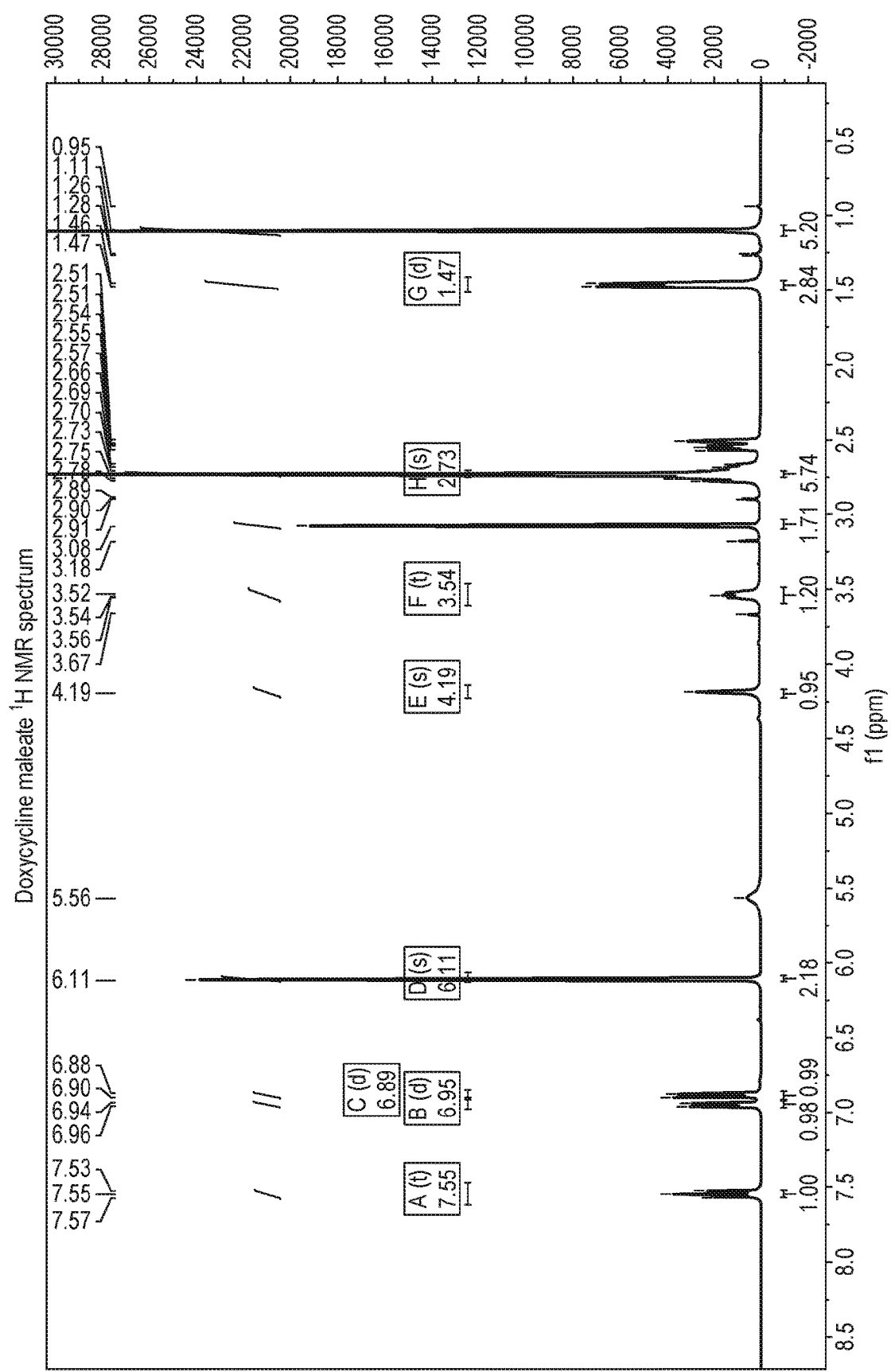
Figure 7:
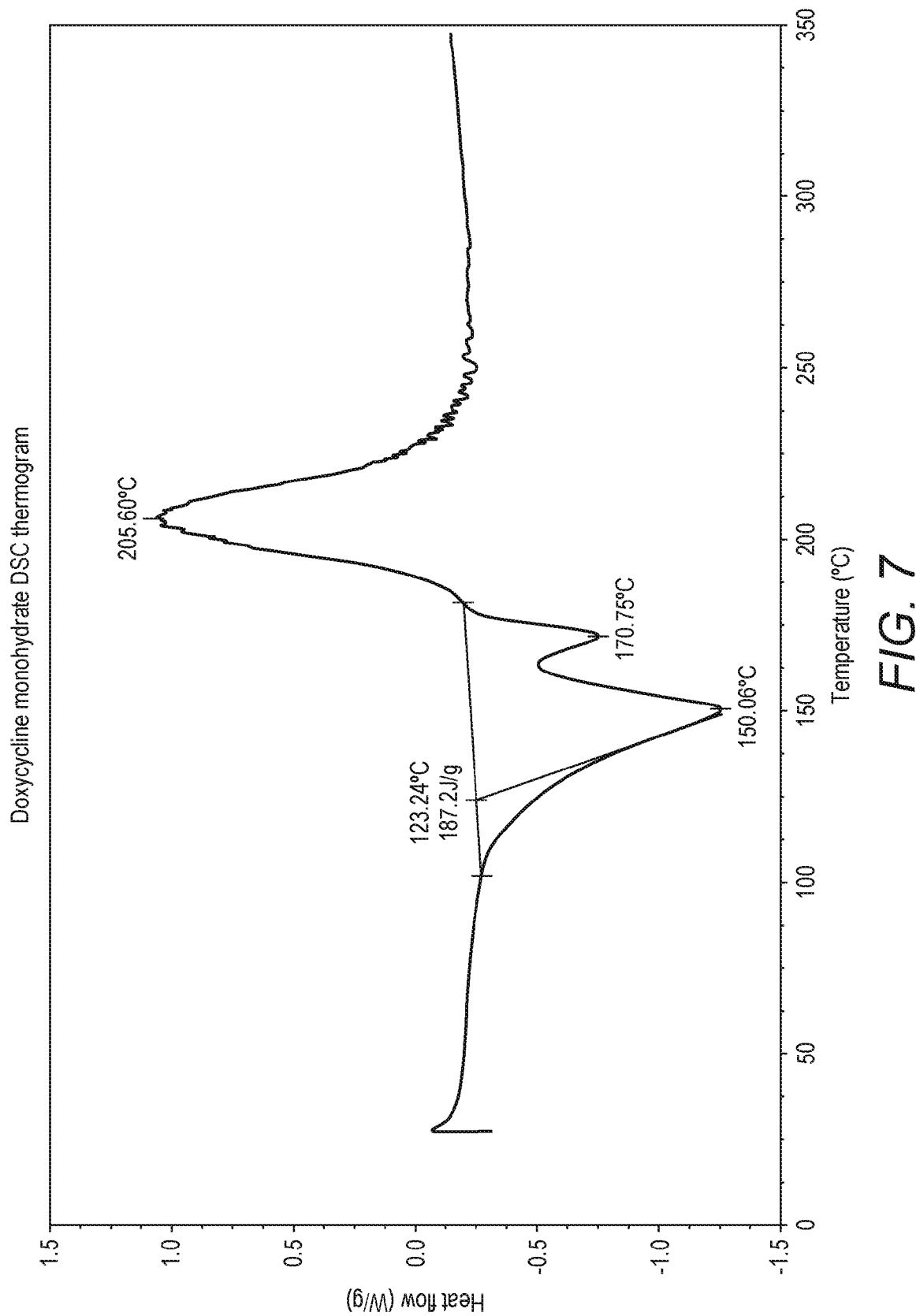
Figure 8:
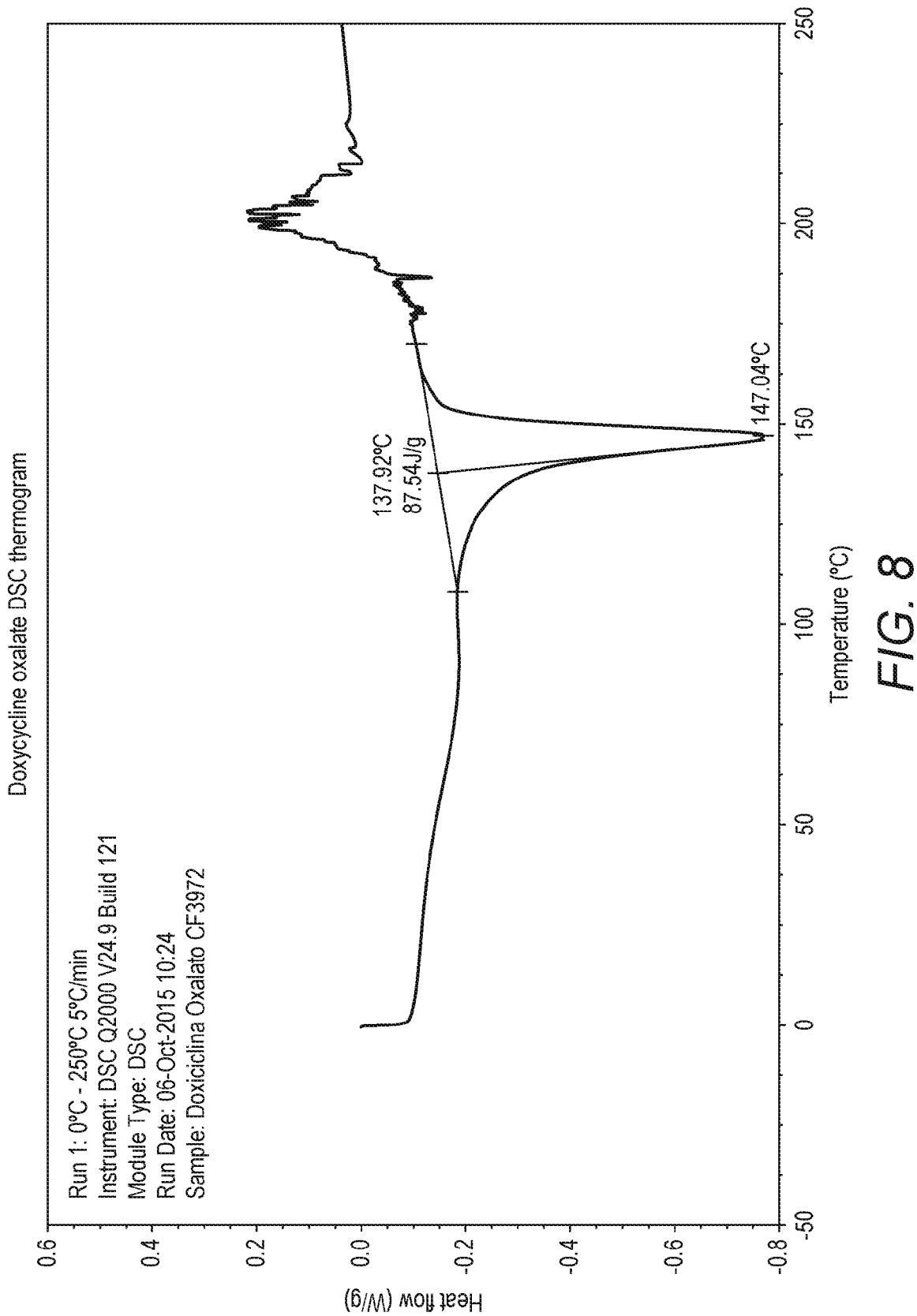
Figure 9:
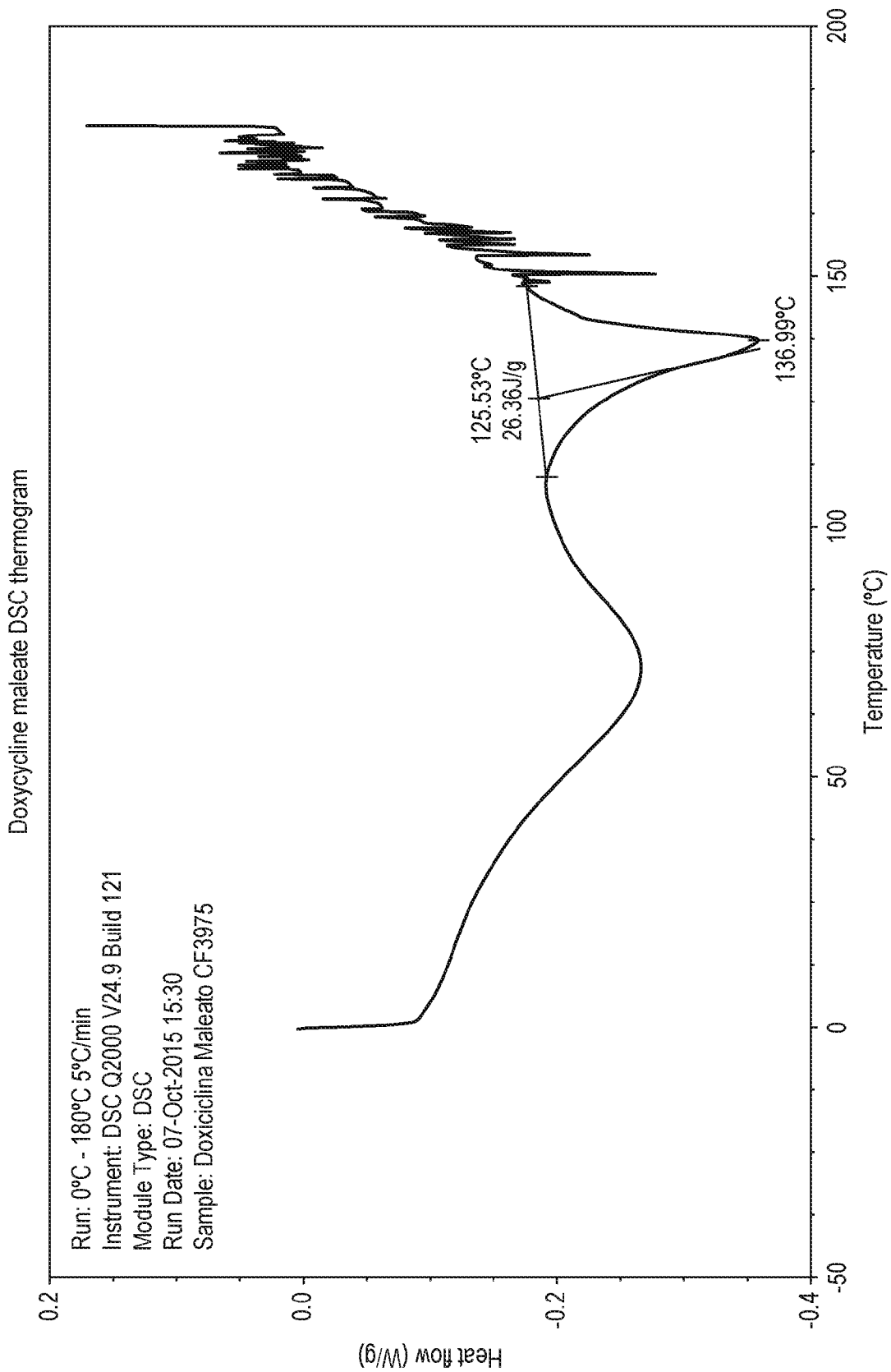
Figure 10:
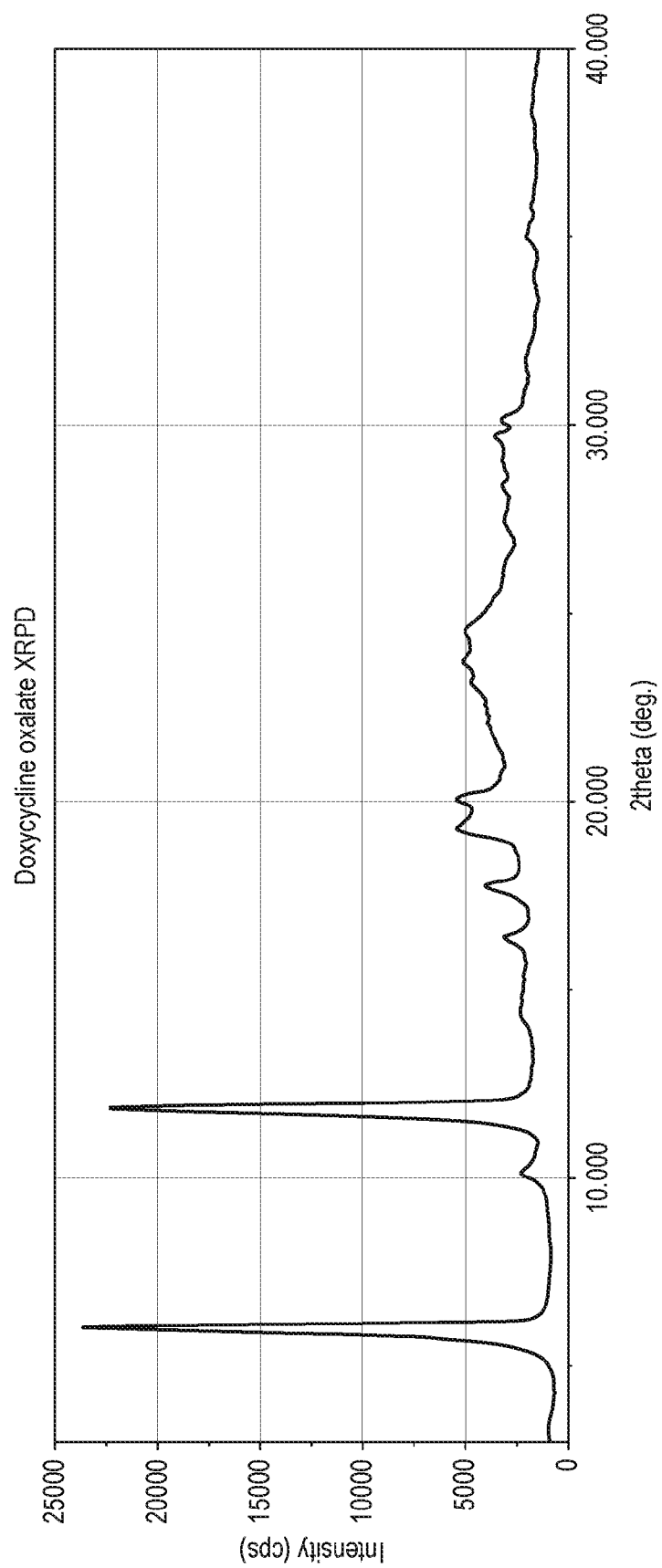
Figure 11:
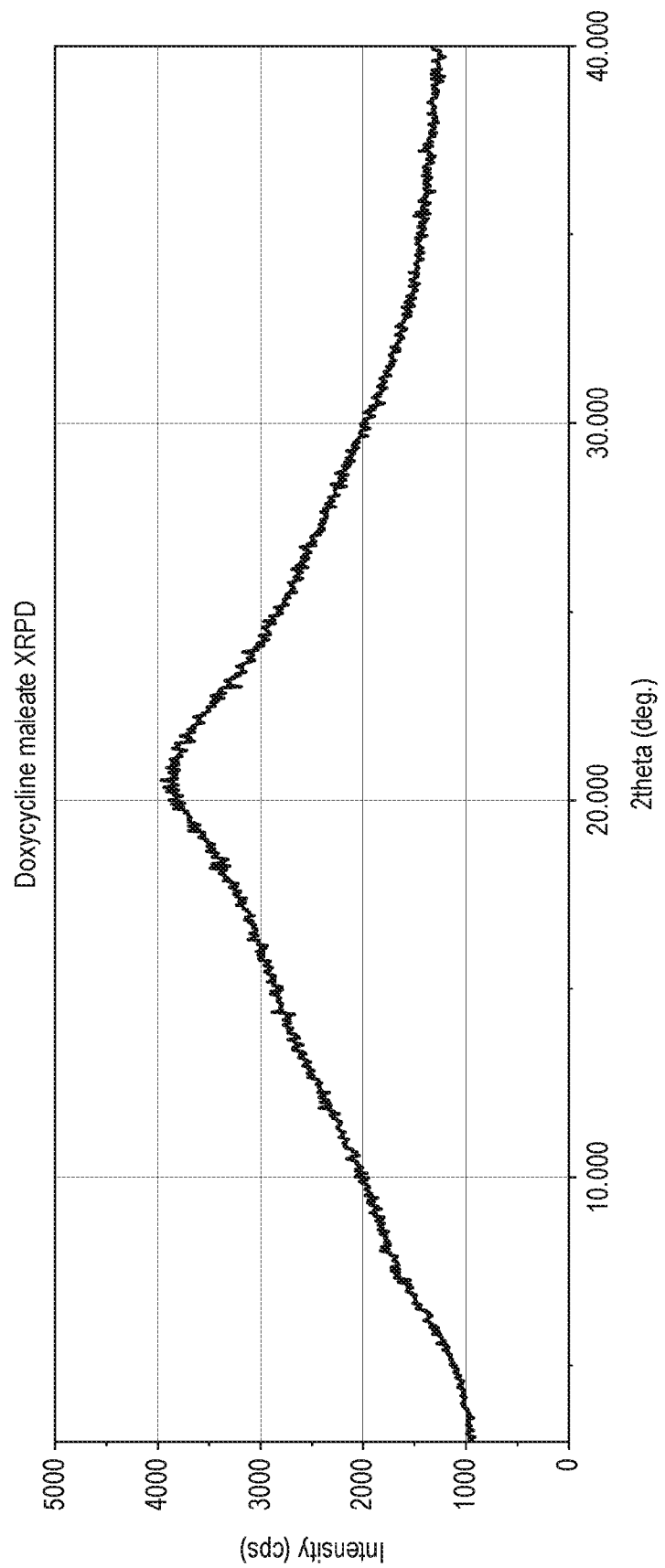
Figure 12:
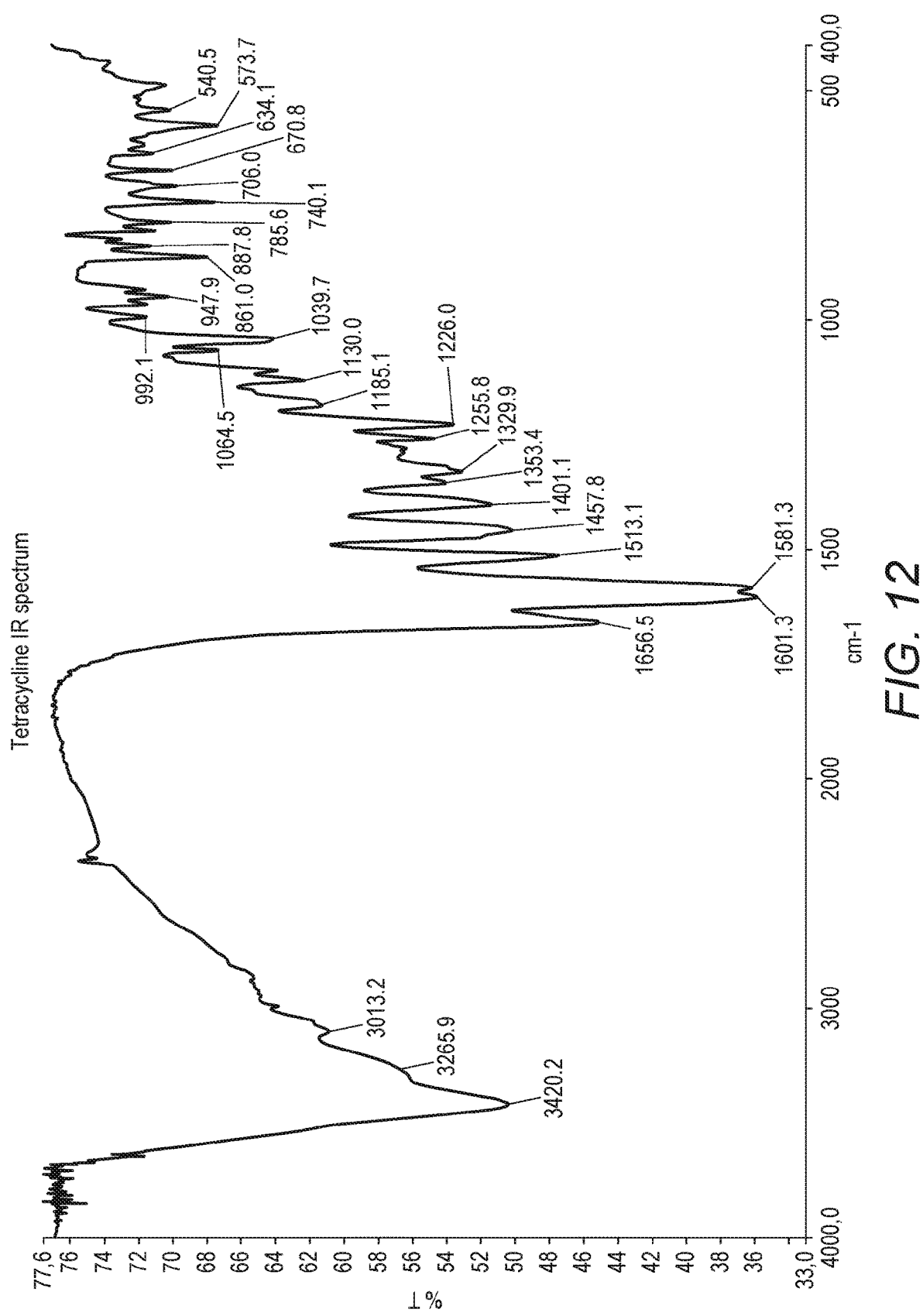
Figure 13:
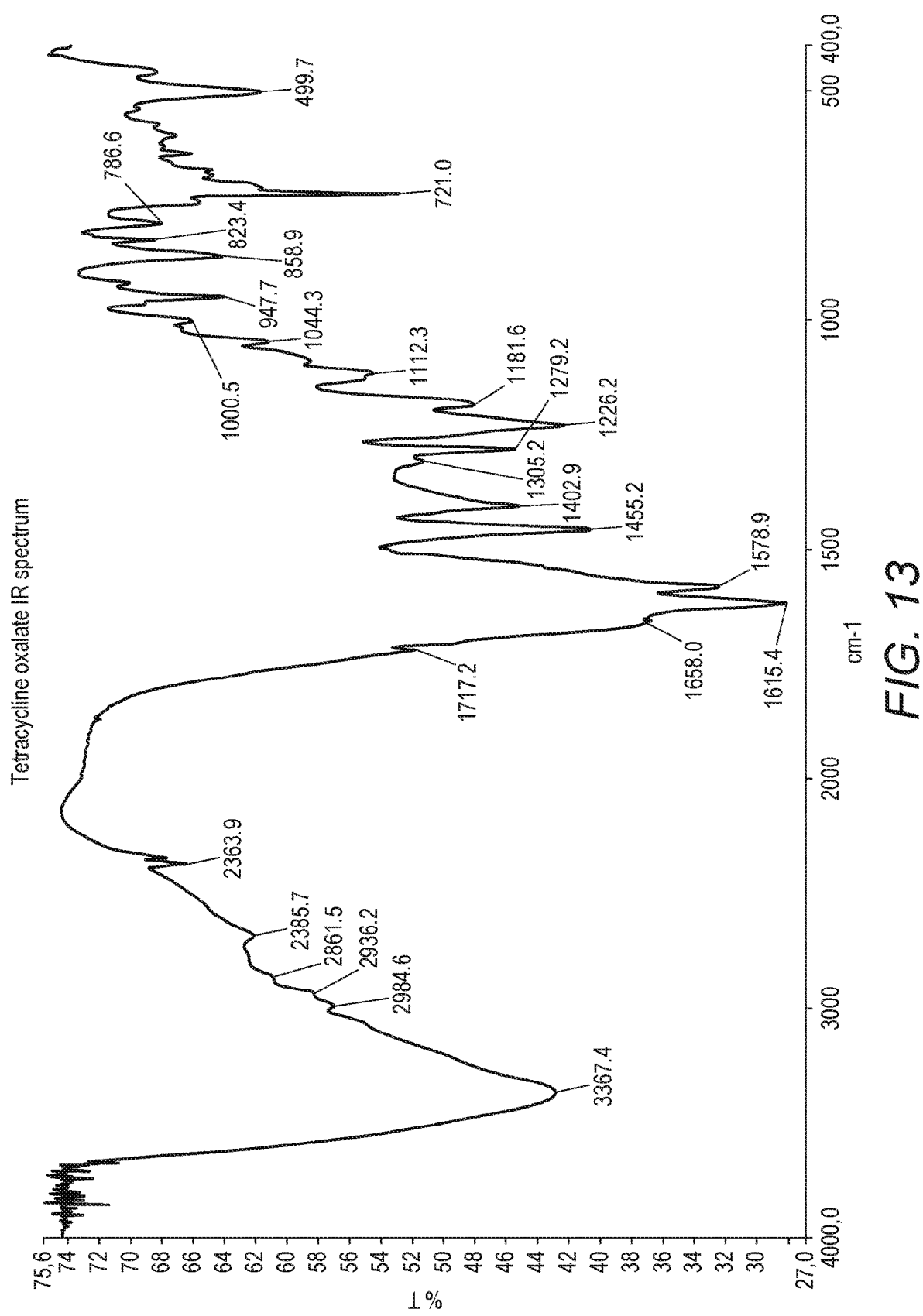
Figure 14:
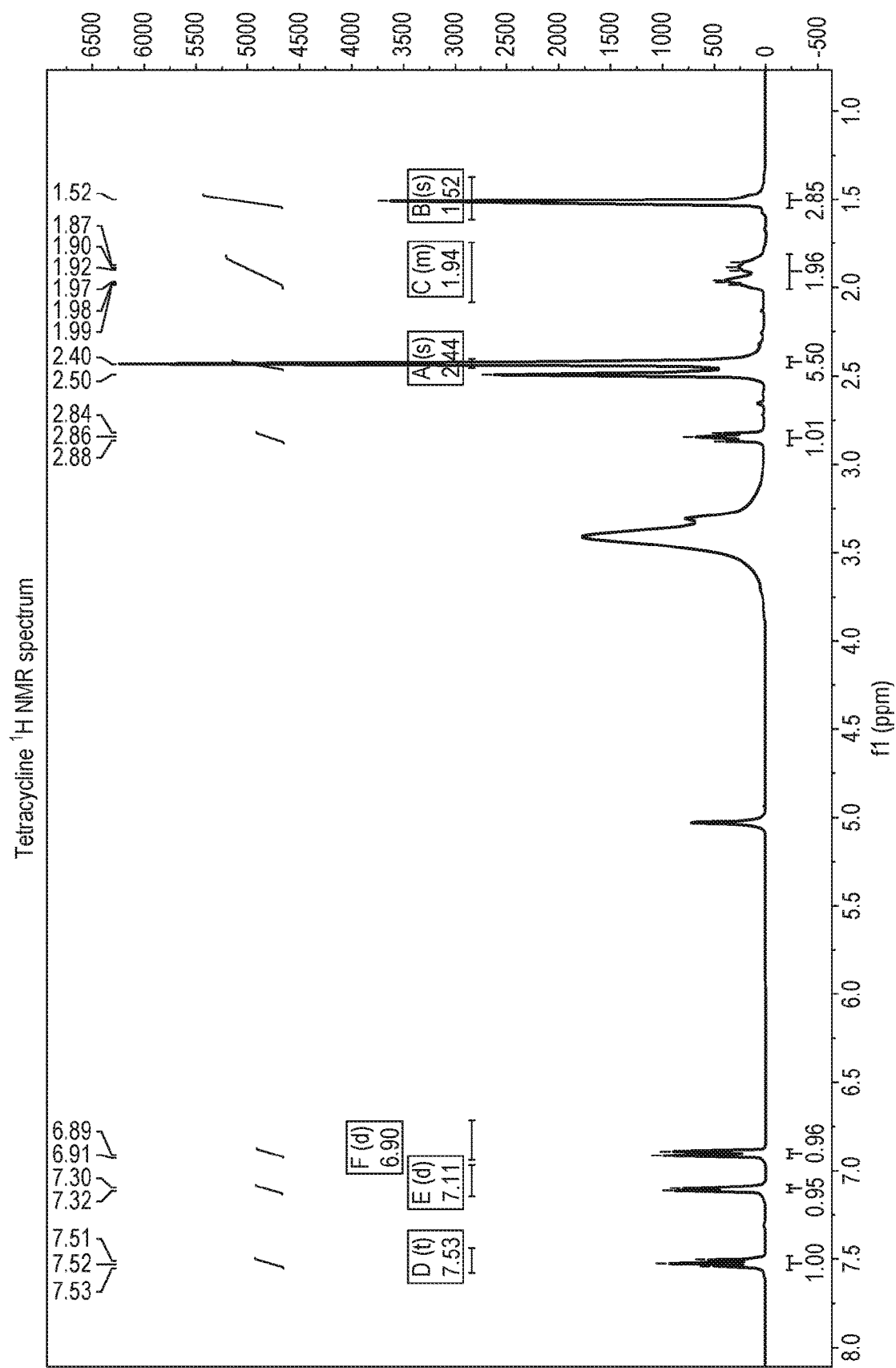
Figure 15:
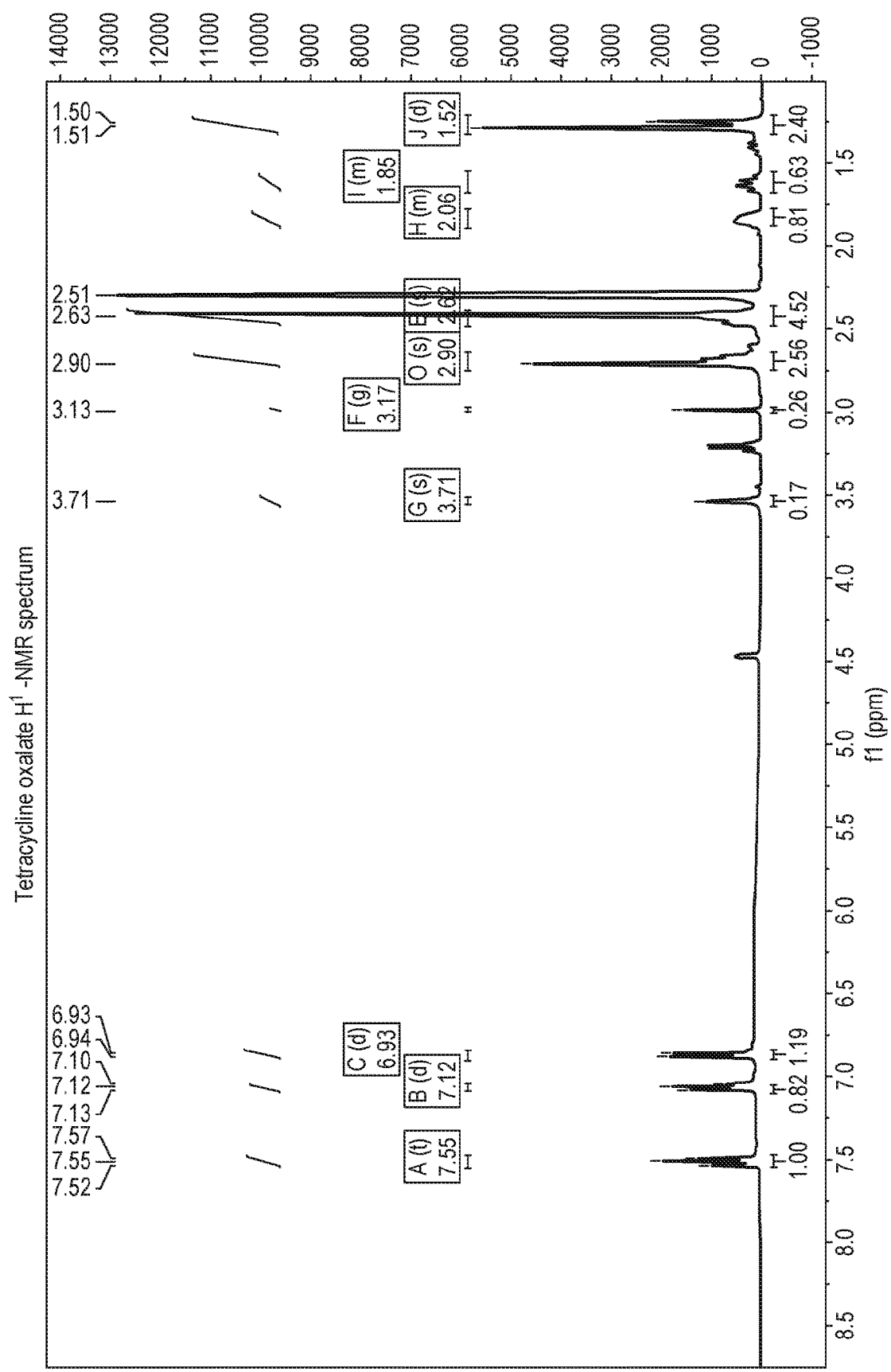
Figure 16:
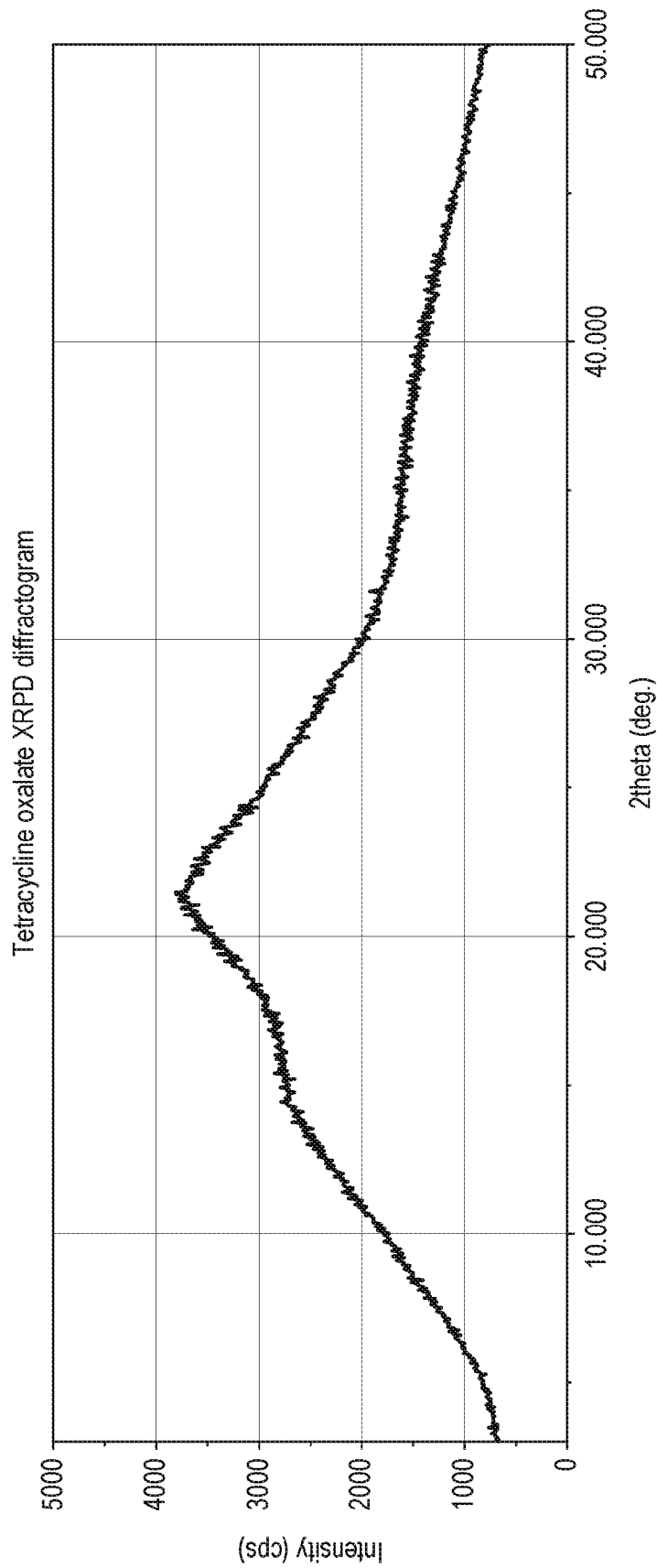
Figure 17:
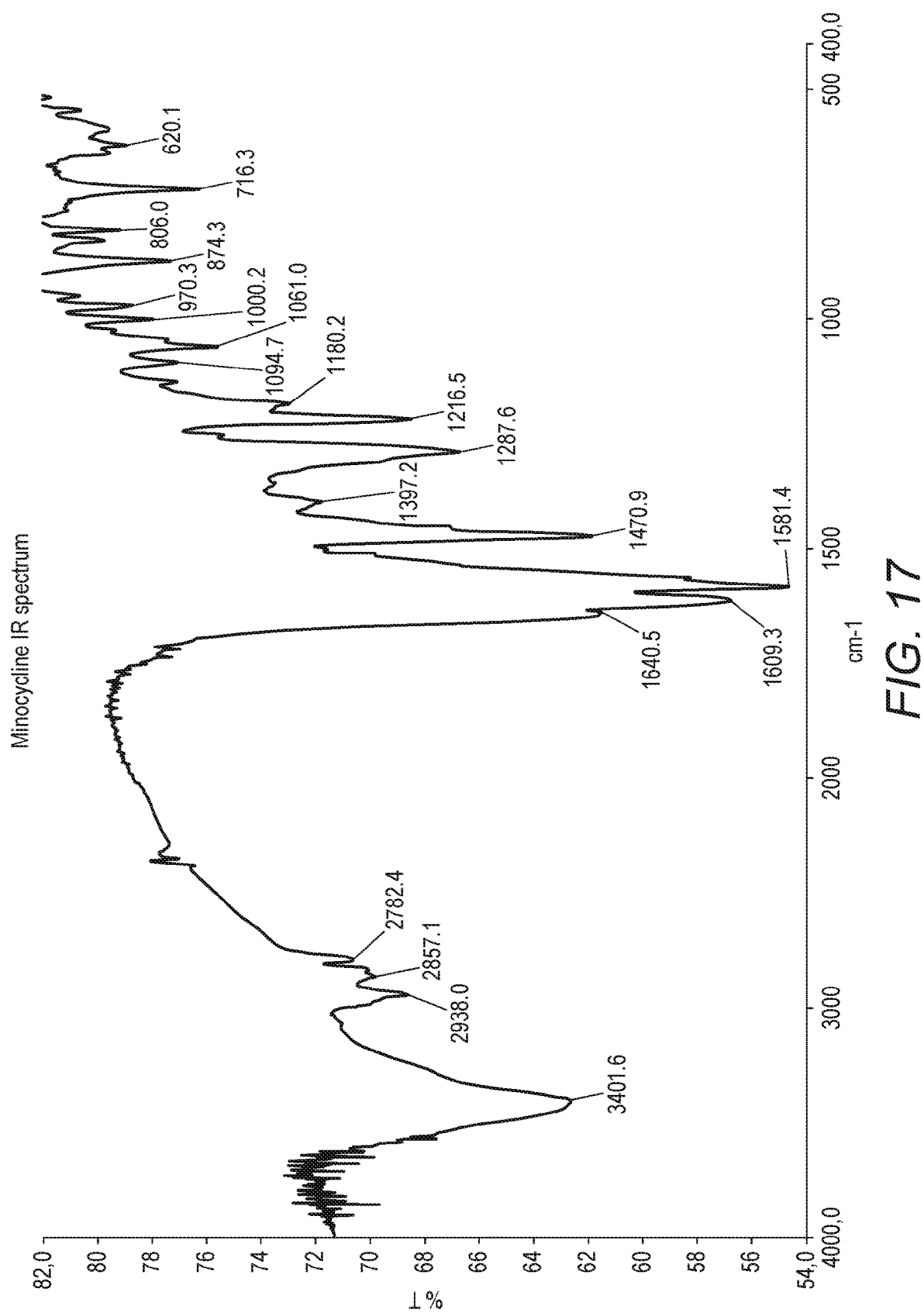
Figure 18:
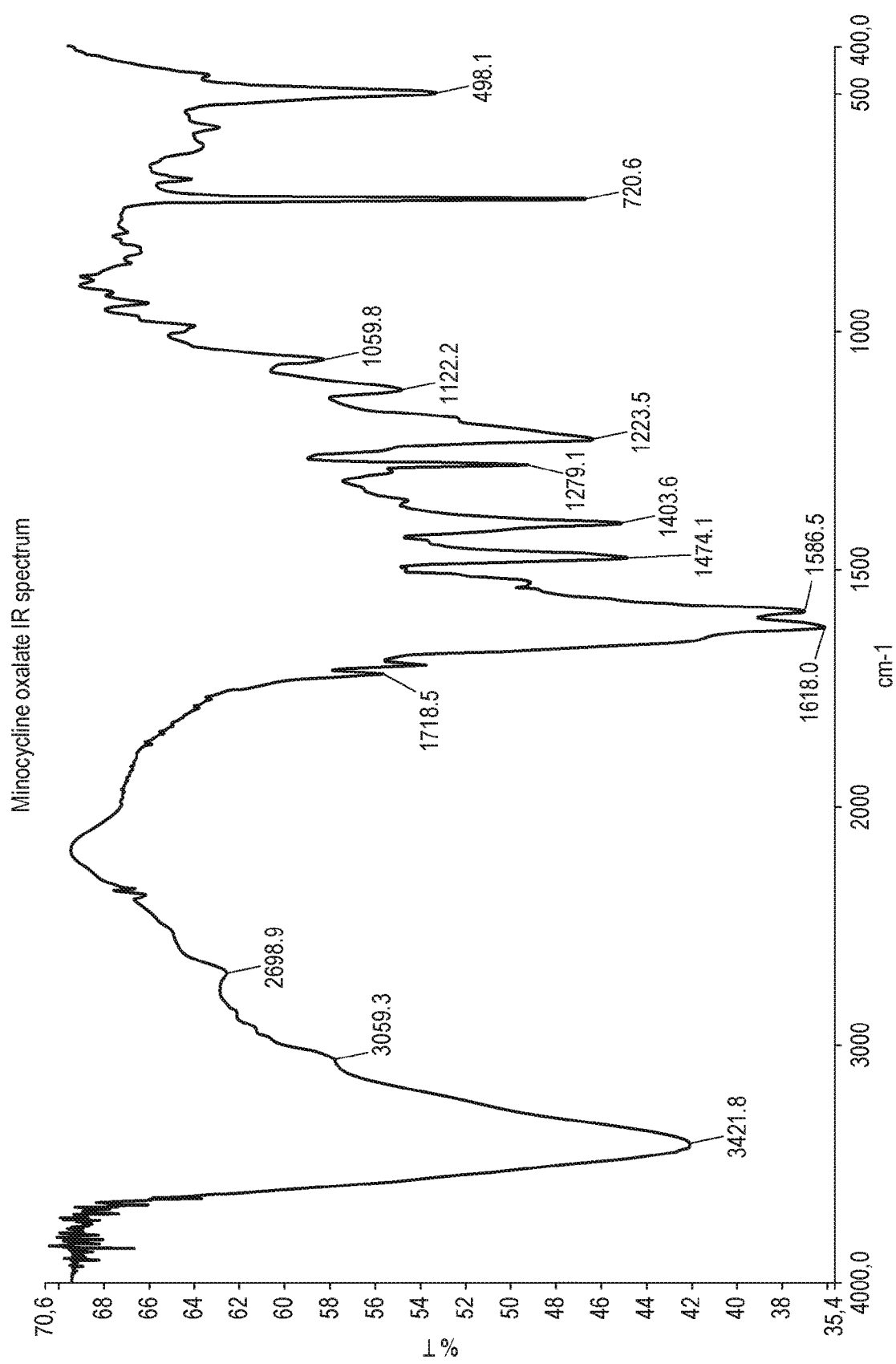
Figure 19:
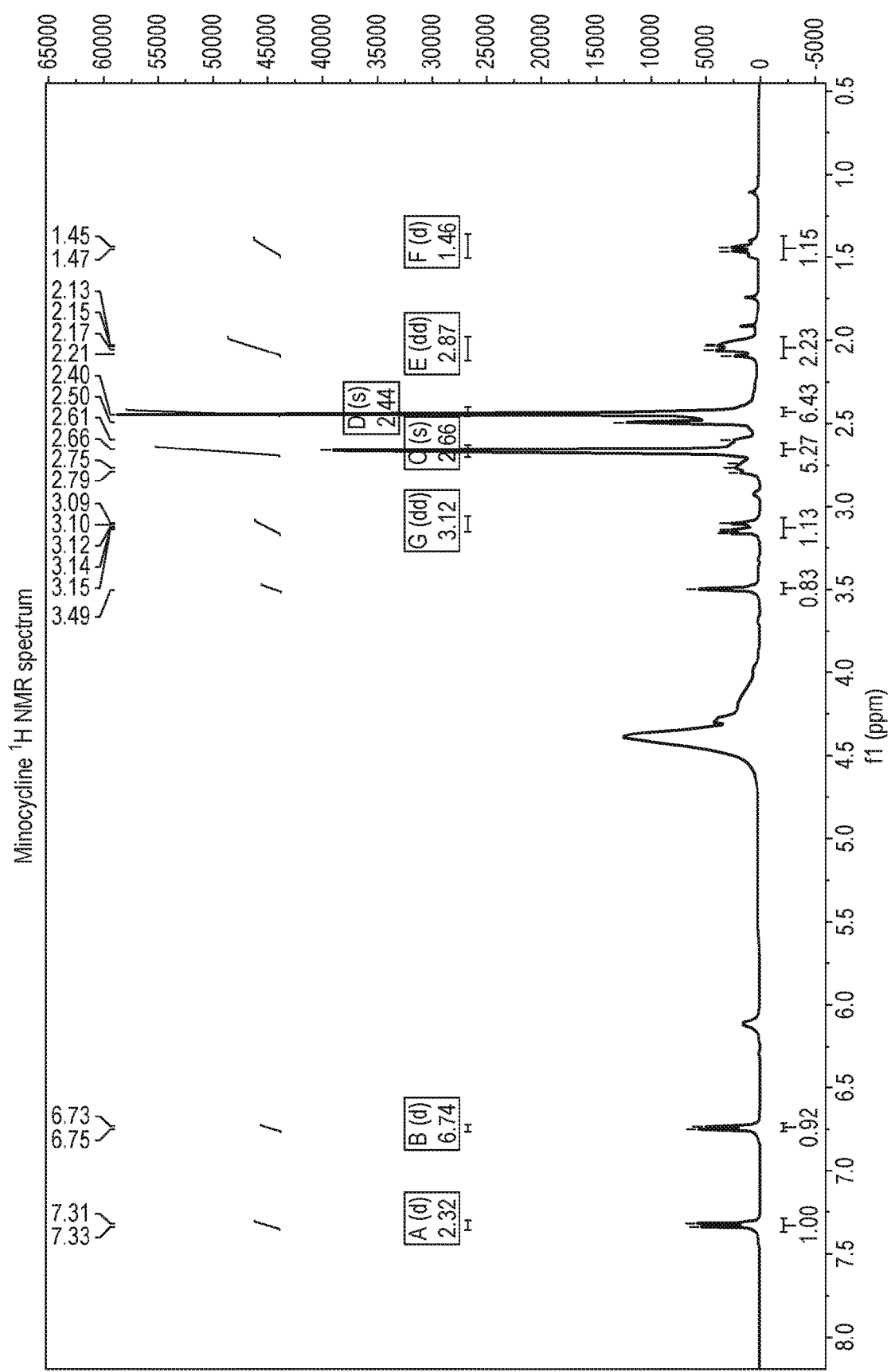
Figure 20:
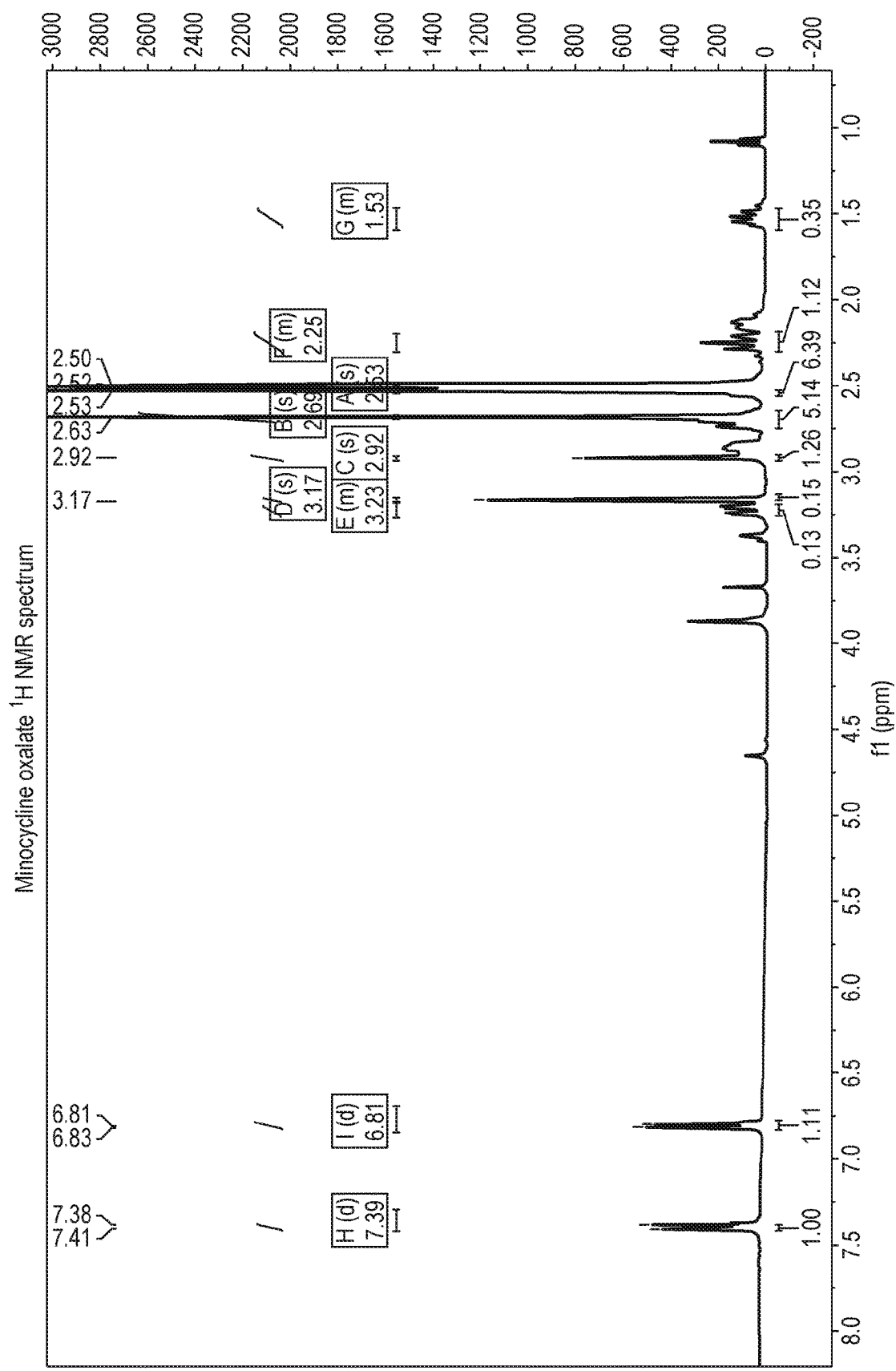
Figure 21:
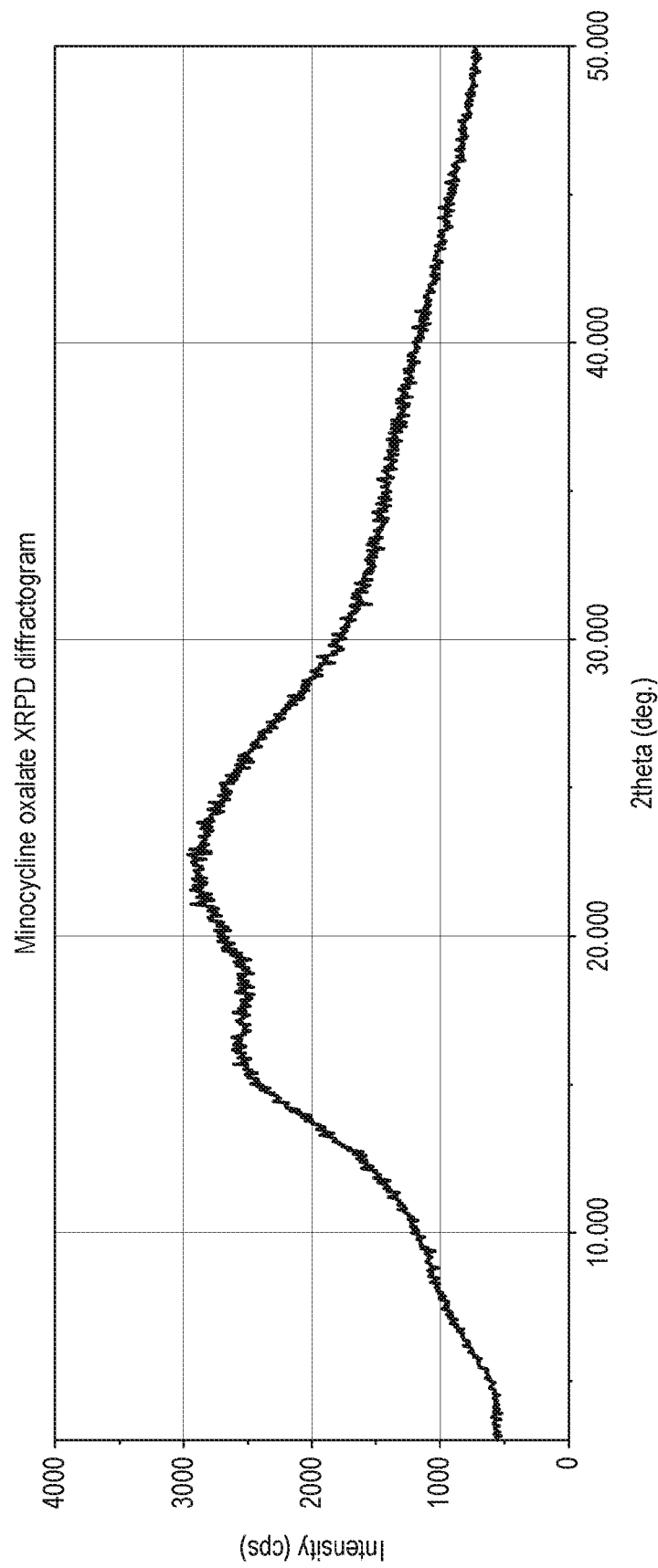
Figure 22:
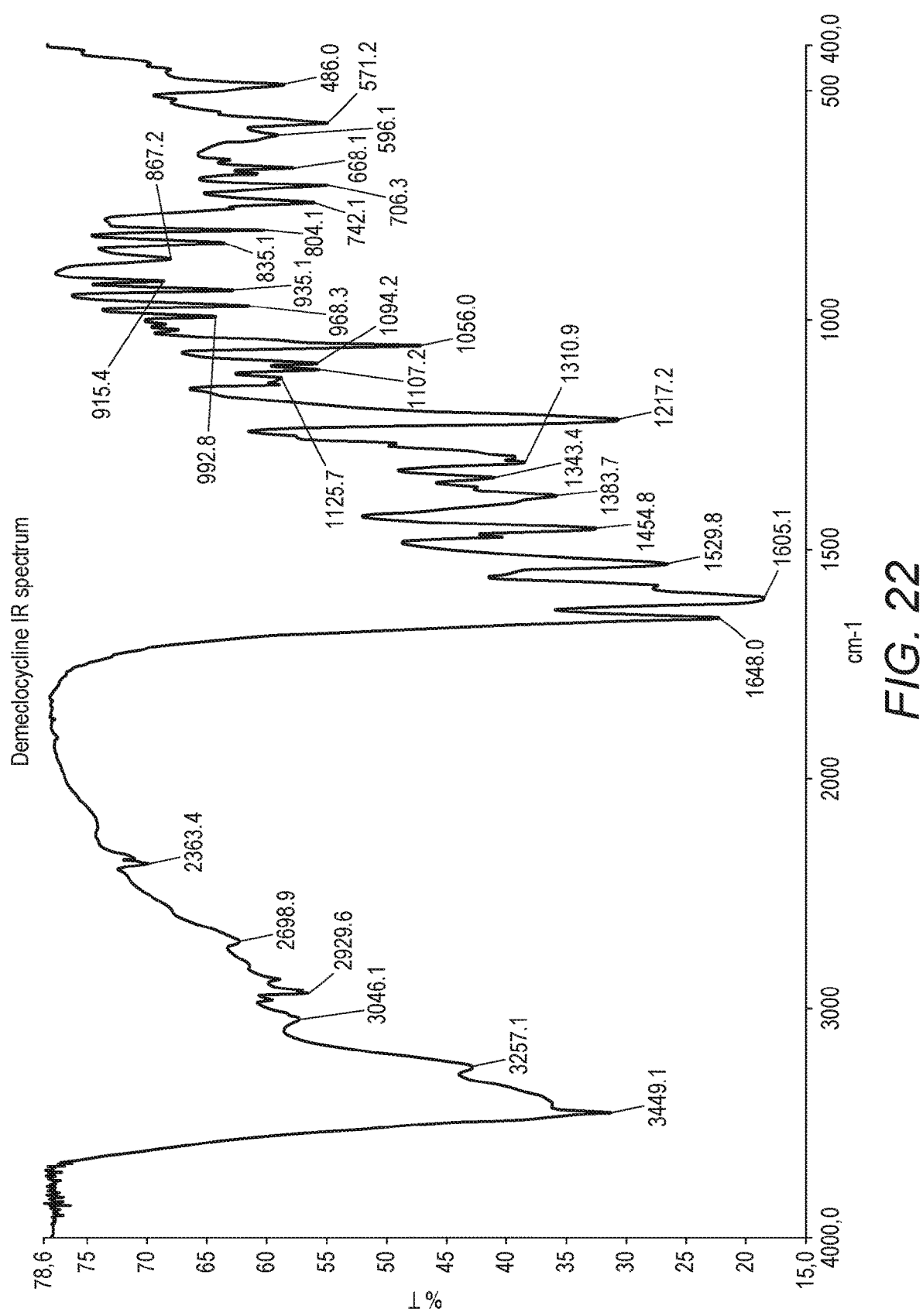
Figure 23:
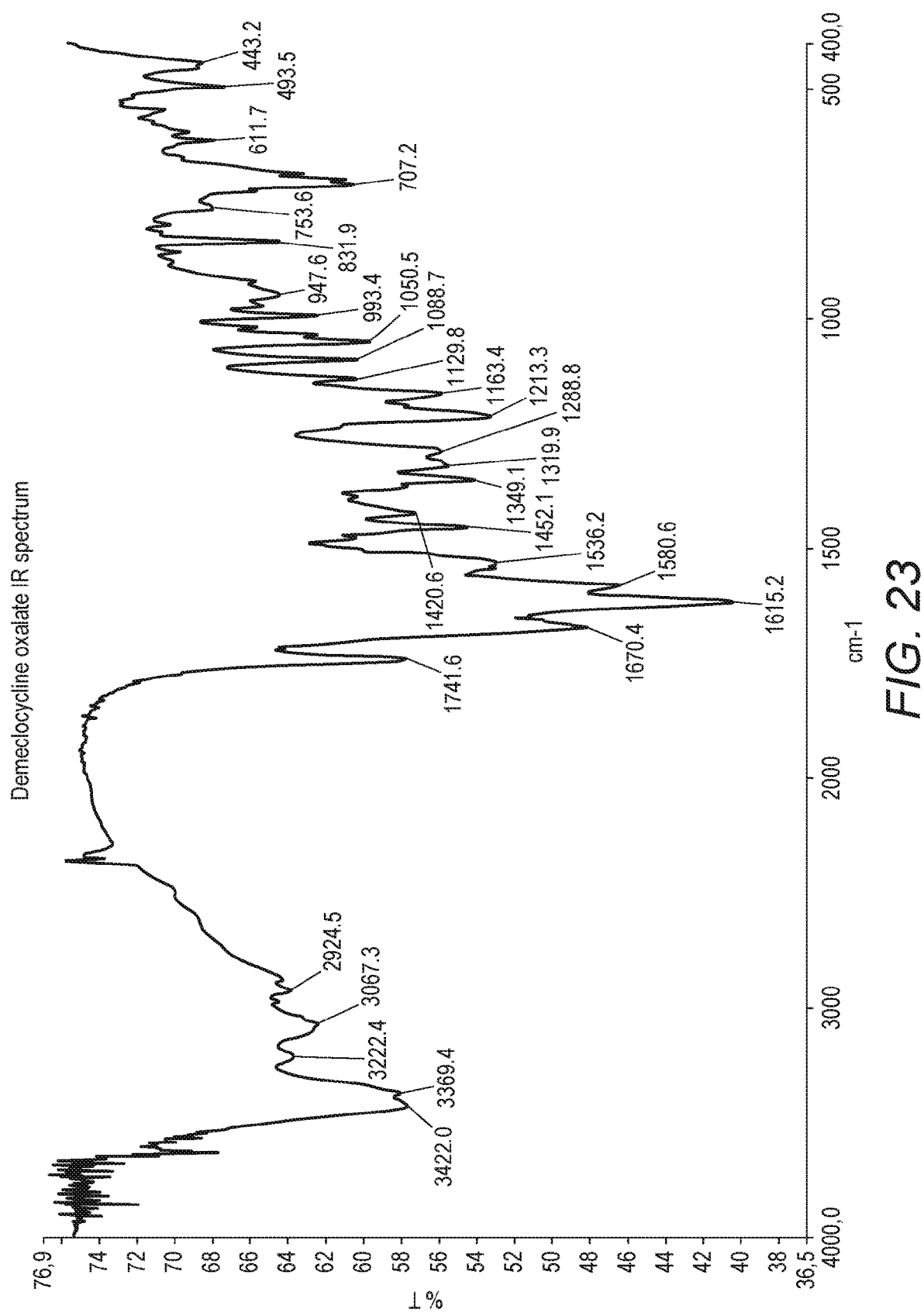
Figure 24:
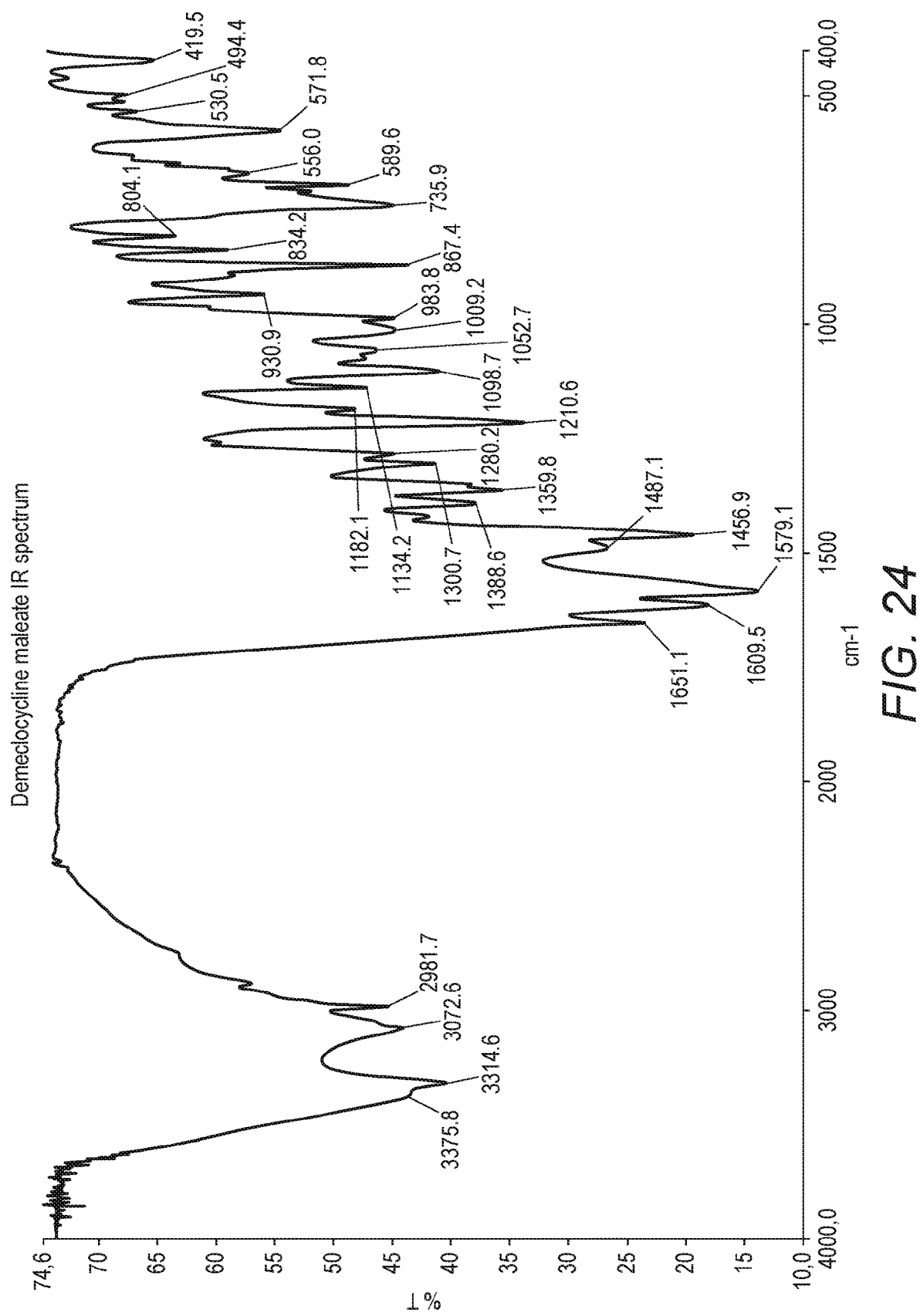
Figure 25:
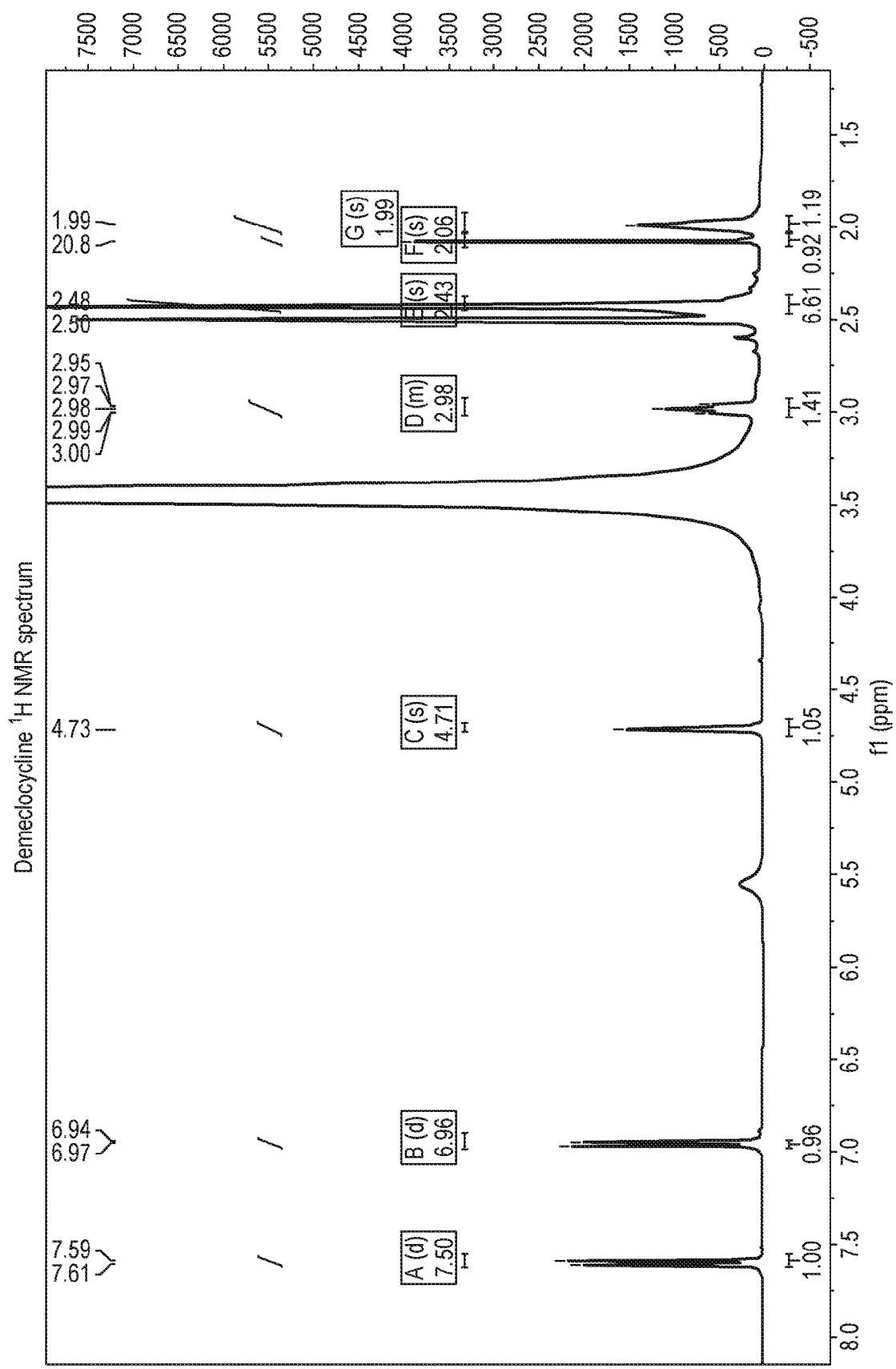
Figure 26:
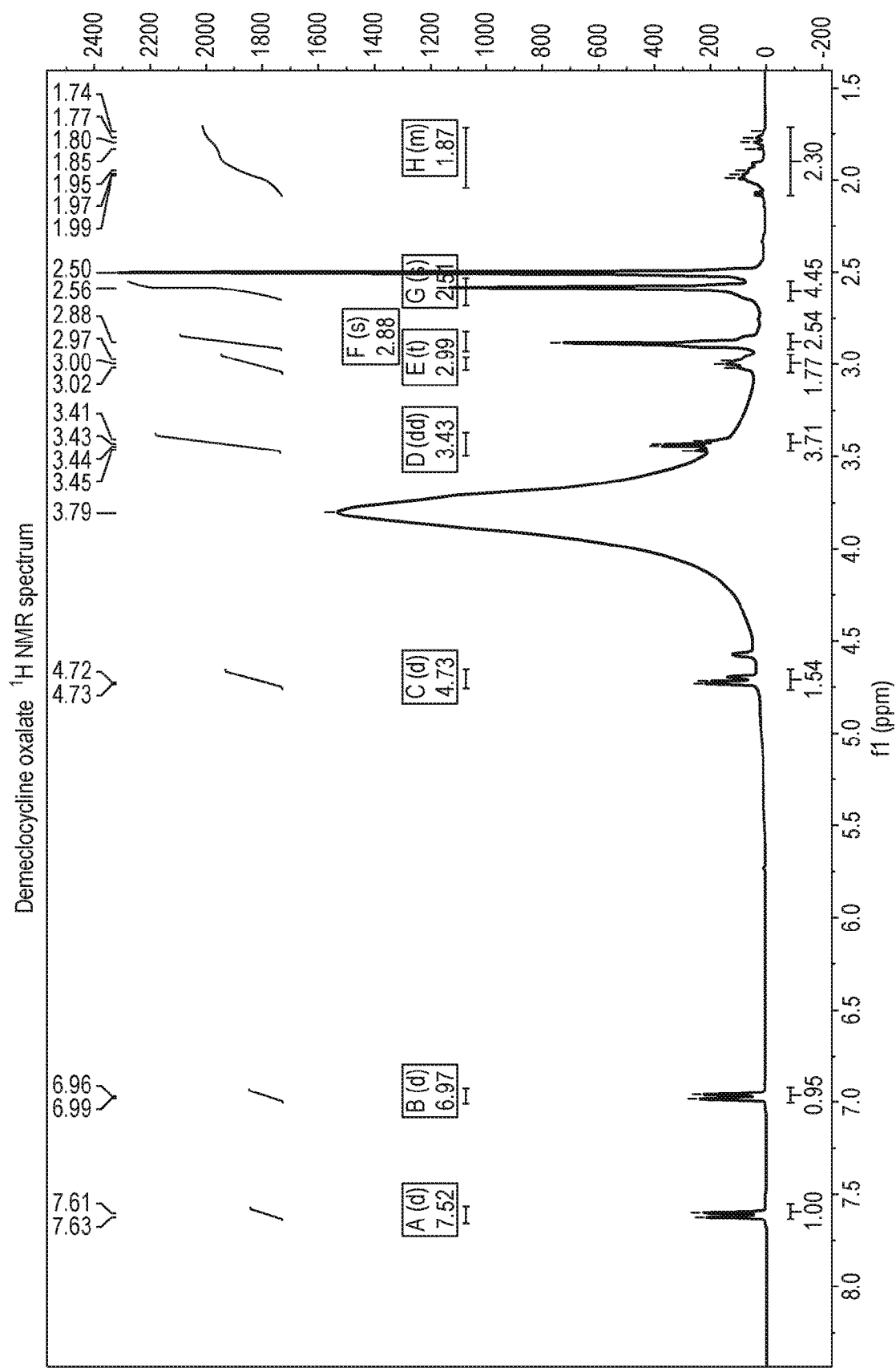
Figure 27:
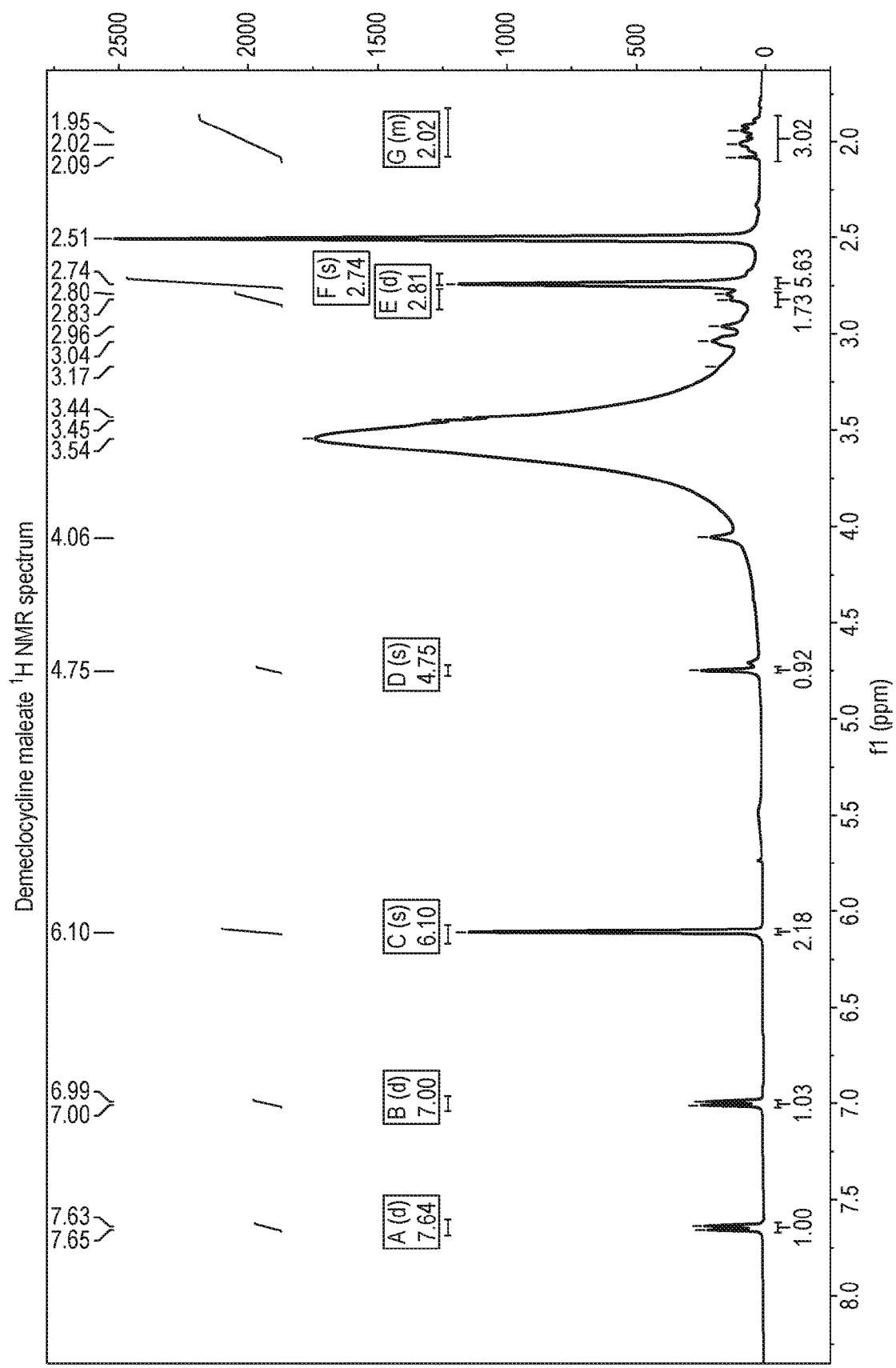
Figure 28:
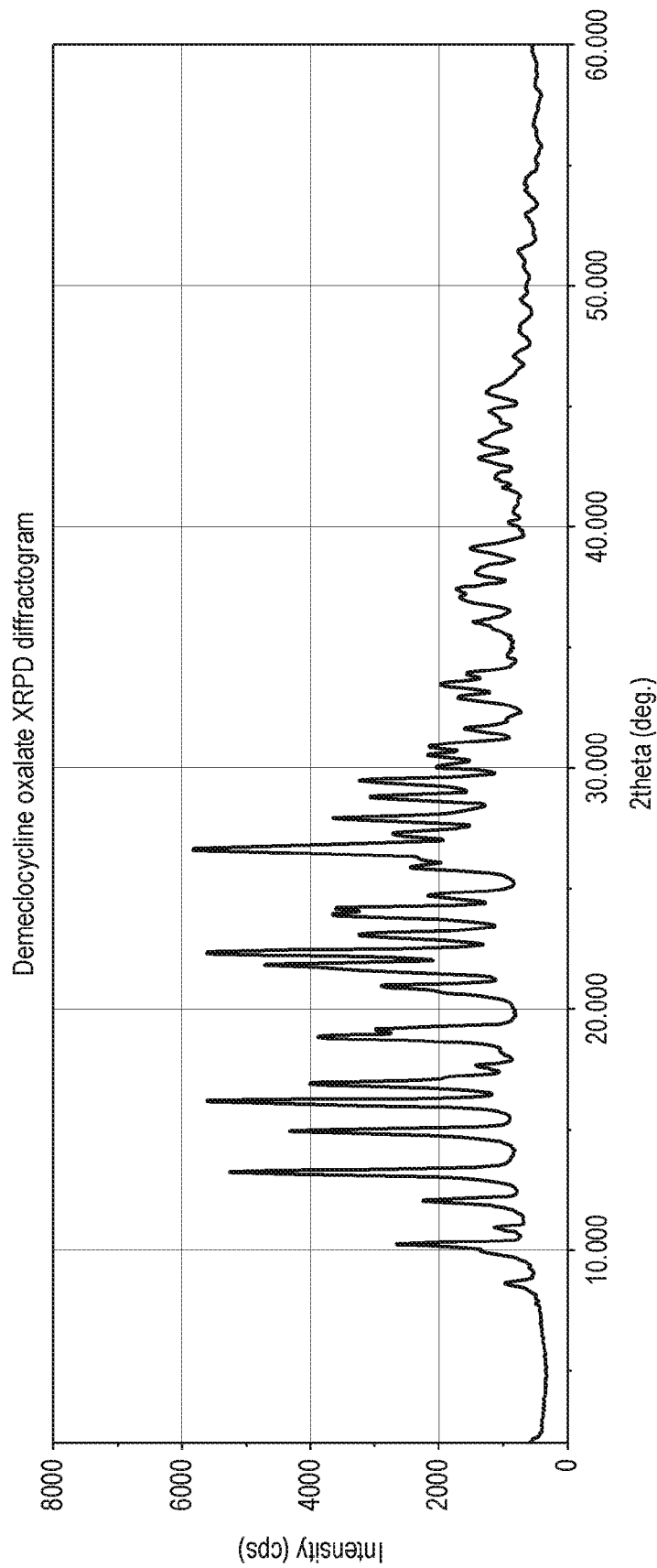
Figure 29:
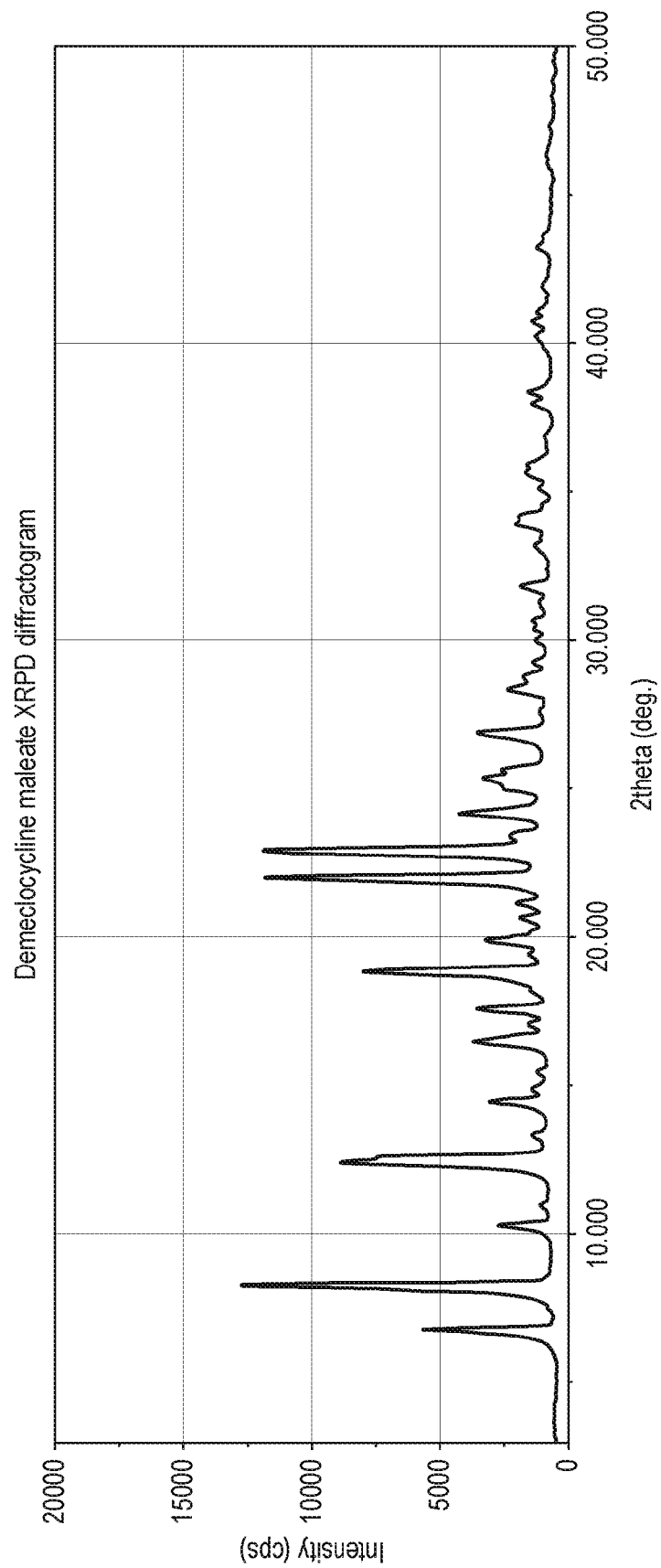

Foreign Communication from a related application—International Preliminary Report on Patentability of International Application No. PCT/GB2016/053695 dated Feb. 26, 2018, 11 pages.

Inoue, Shigeharu, et al., "Molecular Complexes of Tetracycline Acid Salts," Agricultural and Biological Chemistry, vol. 25, No. 4, Jan. 1, 1961, pp. 333-339, XP0556335985.

Leber, Aviva, et al., "Simultaneous Esophageal and Gastric Ulceration Due to Doxycycline Ingestion: Case Report and Review of the Literature," Gastroenterology Research, vol. 5, No. 6, Dec. 2012, pp. 236-238, Elmer Press.

Lim, Lik Thai, et al., "Common eye drops and their implications for pH measurements in the management of chemical eye injuries," International Journal of Ophthalmology, vol. 7, No. 6, Dec. 18, 2014, pp. 1067-1068.

Milne, Christopher-Paul, et al., "The Economics of Pediatric Formulation Development for Off-Patent Drugs," Clinical Therapeutics, vol. 30, No. 11, Nov. 11, 2008, pp. 2133-2145, Excerpta Medica Inc.

Sherman, Alex, et al., "Pill-Induced Gastric Injury," The American Journal of Gastroenterology, vol. 94, No. 2, 1999, pp. 511-513, American College of Gastroenterology.

\* cited by examiner

SALTS OF TETRACYCLINES

CROSS REFERENCE TO RELATED APPLICATIONS

This application is a filing under 35 U.S.C. 371 of International Application No. PCT/GB2016/053695 filed Nov. 24, 2016, entitled "Salts of Tetracyclines" which claims priority to Portuguese Patent Application No. 108978 filed Nov. 24, 2015, which applications are incorporated by reference herein in their entirety.

FIELD OF INVENTION

The present invention relates generally to tetracycline compounds, in particular to salts thereof, and more particularly to certain new salts of tetracyclines. The invention also relates to a method of preparing tetracycline compounds, in particular salts thereof, and to pharmaceutical formulations and medical devices incorporating such compounds, and to their use in medicine.

BACKGROUND OF THE INVENTION

Doxycycline, also designated by α-6-deoxy-5-hydroxytetracycline or by α-6-deoxyoxytetracycline, is a semi-synthetic broad spectrum antibiotic of molecular structure (I) disclosed for the first time in the U.S. Pat. No. 3,019,260.

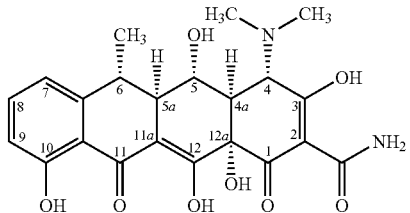
(I)

The U.S. Pat. No. 3,019,260 discloses the preparation of salts of doxycycline by addition of acids to doxycycline until a pH of less than 4. Salts of the acids hydrochloric, sulfate, phosphate, trichloroacetate, oxalate, citrate, gluconate are referred to be prepared according to the general procedure taught by the authors.

The U.S. Pat. No. 3,200,149 discloses the preparation of 6-epi-doxycycline (II) and in example XXXIX discloses the preparation of salts of 6-epy-6-deoxy-5-oxy-tetracycline such as the hydrochloric, hydroiodic, hydrobromic, phosphoric, metaphosphoric, nitric and sulfuric acids as well as salts of organic acids such as tartaric, acetic, citric, malic, benzoic, glycolic, gluconic, gulonic, succinic, arysulfonic.

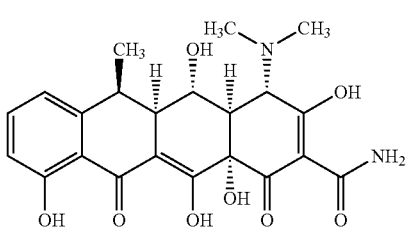
(II)

The salts are prepared by dissolving 6-epi-6-deoxy-5-oxy-tetracycline in methanol containing an equimolar amount of the acid. The salts are precipitated by addition of ether to the methanolic solution and are isolated by filtration and drying. No analytical data supporting the salts formation is presented neither the yield is reported. The scope of this patent was to disclose 6-epi-6-deoxytetracyclines, D-ring substituted analogs, 11α-substituted analogs and D-ring-11α-substituted analogs as well as the method of producing these compounds. The inventors use the designations "6-epi" and "a" interchangeably to refer to 6-epi-6-deoxy tetracyclines.

The patent GB1228629 discloses the use of doxycycline salts to prepare aqueous solutions with polyvinylpyrrolidone for parenteral, oral and topical administration. The salts used were the hydrochloride, hydrobromide, sulfate, nitrate, ascorbate, citrate, gluconate, lactate, isonicotinate, gentisinate, pantothenate, salicylate, glucoronate, formate and glutamate. The inventors argued that these solutions were surprisingly stable and topically well tolerated.

The patent BE896423 discloses alkyl sulfate salts of doxycycline of formula (III) where R is an alkyl radical, saturated or unsaturated, linear or branched chain, with 6 to 18 carbon atoms.

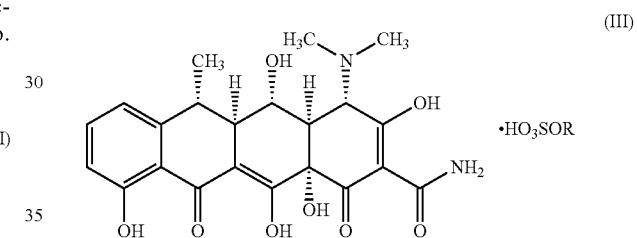
(III)

The salts are prepared by treating doxycycline base with a stoichiometric amount of the alkylsulfuric acid or by reacting an inorganic salt of doxycycline with an alkaline or ammonium salt of the alkylsulfuric acid. In both cases the preparation is carried out in water or in aqueous alcohol solutions. According to the inventors, the alkyl sulfate groups decrease the surface tension of doxycycline and increase the liposolubility, the powder dispersion as well as the wettability effect.

The U.S. Pat. No. 3,932,490 discloses doxycycline aceturate (IV) and its preparation by reaction of doxycycline with the aceturic acid (acetylaminoacetic acid).

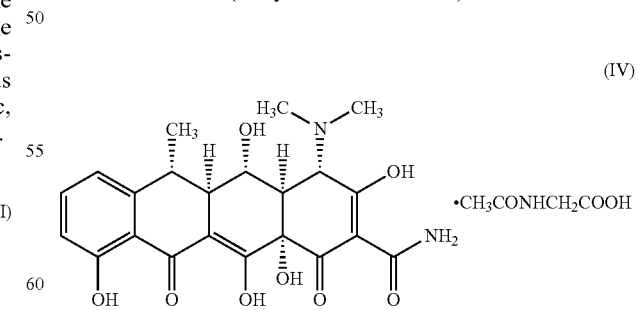
(IV)

To prepare the salt the inventors treat a solution of doxycycline with a solution of an equimolar amount of acetylamino acetic acid and isolate the product by evaporation of the solvent or by lyophilization of the reaction mixture. The product is characterized by elemental analysis, melting point, solubility and infrared in Nujol. The invention teaches that doxycycline aceturate is more soluble in water than doxycycline and therefore is more suitable for parenteral administration.

The U.S. Pat. No. 4,877,559 discloses the preparation of doxycycline p-toluenesulfonate, compound of formula (Y), by addition of p-toluenesulfonic acid to the solution of doxycycline obtained by hydrogenation of methacycline, in a solvent which is a non-solvent for the salt, for example, methanol.

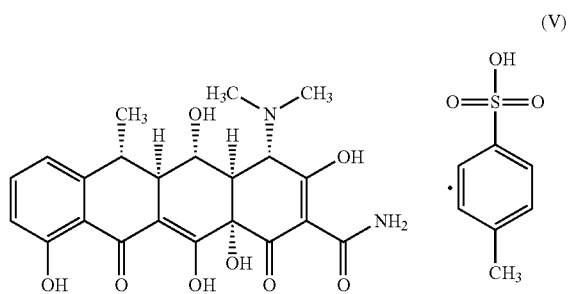 [SMILES: C[C@H]1c2cccc(O)c2C(=O)C2=C(O)[C@]3(O)C(=O)C(C(N)=O)=C(O)[C@@H](N(C)C)[C@@H]3[C@@H](O)[C@@H]21 ; Cc1ccc(S(=O)(=O)O)cc1]

(V)

The product obtained was characterized by circular paper chromatography.

Minocycline, compound of formula (VI), also designated by 7-dimethylamino-6-demethyl-6-deoxytetracycline, is a semi-synthetic broad spectrum antibiotic of molecular structure (I) disclosed in the U.S. Pat. No. 3,226,436.

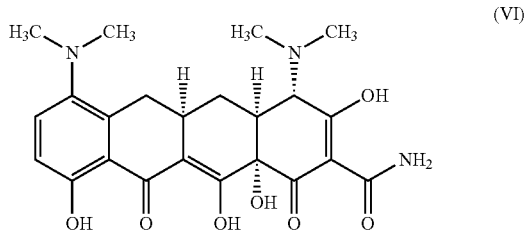 [SMILES: CN(C)c1ccc(O)c2c1C[C@H]1C[C@H]3[C@H](N(C)C)C(O)=C(C(N)=O)C(=O)[C@@]3(O)C(O)=C1C2=O]

(VI)

This patent refers to the prophetic preparation of the hydrochloride, sulfuric and trichloroacetic salts of minocycline.

The patent application US20090099376 refers to the use of minocycline salts of acetic, benzoic, maleic and succinic acids, among others, in the preparation of tigecycline, but it does not disclose minocycline oxalate salt. No description on the preparation of the above salts is provided neither analytical data showing the characterization of the mentioned salts is presented.

Tetracycline, compound of formula VII, formerly designated by omegamycin, is an antibiotic produced by fermentation.

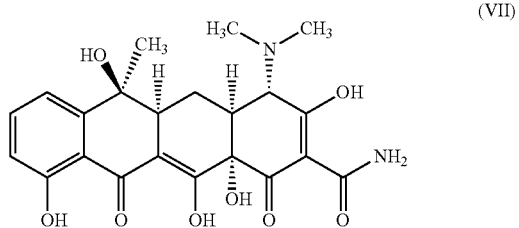 [SMILES: CN(C)[C@@H]1C(O)=C(C(N)=O)C(=O)[C@@]2(O)C(O)=C3C(=O)c4c(O)cccc4[C@@](C)(O)[C@H]3C[C@@H]12]

(VII)

The U.S. Pat. No. 2,886,595 refers to the preparation of salts of tetracycline such as the citrate, the tartaric, the benzoate, the acetate, the succinate, among others but not to the oxalate salt. General procedures are referred to prepare the salts such as the pH adjustment of a solution of tetracycline to a point just below that at which the antibiotic begin to separate, adding stoichiometric amounts of acid to a solution of tetracycline base in water or organic solvent, to form the acid addition salt. The solid salt is isolated by evaporation of the salt solution, or by lyophilization, or by collecting the precipitated salt by filtration, or by precipitating the salt by addition of another organic solvent. The examples given describe the extraction of tetracycline from fermentation broth and described only the preparation of tetracycline hydrochloride and tetracycline formate. These salts are characterized only by melting point.

Demeclocycline (VIII), also known as 7-chloro-6-demethyltetracycline, an antibiotic manufactured by fermentation was disclosed in the U.S. Pat. No. 2,878,289.

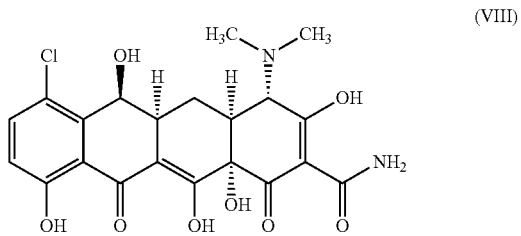 [SMILES: CN(C)[C@@H]1C(O)=C(C(N)=O)C(=O)[C@@]2(O)C(O)=C3C(=O)c4c(O)ccc(Cl)c4[C@@H](O)[C@H]3C[C@@H]12]

(VIII)

The U.S. Pat. No. 2,878,289 refers that demeclocycline form salts of the same type and in general manner as do the tetracyclines and that the acid salts can be formed by treatment of demeclocycline with acids of pH less than about 4. The authors refer to the acetate salt and other organic salts but did not specify further organic salts besides acetate neither give examples on how to prepare them. No examples, neither detailed descriptions are given on the preparation of organic salts of demeclocycline.

Sancycline, also designated by 6-Demethyl-6-deoxy-tetracycline (IX), a semi-synthetic antibiotic was disclosed in the U.S. Pat. No. 3,019,260.

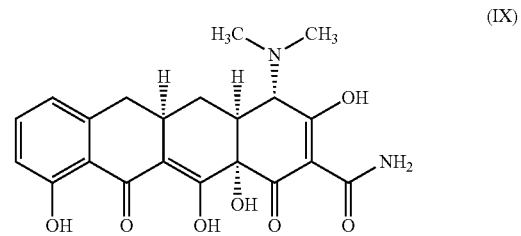 [SMILES: CN(C)[C@@H]1C(O)=C(C(N)=O)C(=O)[C@@]2(O)C(O)=C3C(=O)c4c(O)cccc4C[C@H]3C[C@@H]12]

(IX)

The U.S. Pat. No. 3,019,260 refers to the preparation of acid salts such as trichloroacetate, citrate, oxalate, among others but does not refer to the maleate salt. The inventors refer that the mineral acid salts of the tetracyclines therein disclosed can be prepared by treatment with acids such as hydrochloric acid at pH less than about 4 and that the acid salts such as the sulfate, phosphate, trichloroacetate, oxalate, citrate and gluconate may be formed in a similar manner. The examples teach how to obtain the hydrochloride salt but do not teach how to prepare the organic acid salts neither a description on the preparation of these salts is provided.

The patent GB901209 discloses polyvalent metal salts complexes of sancycline and refer in example V to the preparation of acid addition salts of sancycline by adding mineral acids to methanolic solution of sancycline. The salts are isolated by evaporation of the aqueous solution or by addition of a non-solvent. The hydrochloride, the hydrobromide, the sulfate, the nitrate, the subsalicylate, the phosphate and the tannate (in example VII) salts are prepared according to the example. No disclosure is made with respect to the maleate acid addition salt.

Lymecycline, compound of formula X, also designated by N-lysinomethyltetracycline, is a semi-synthetic antibiotic derived from tetracycline.

(X)
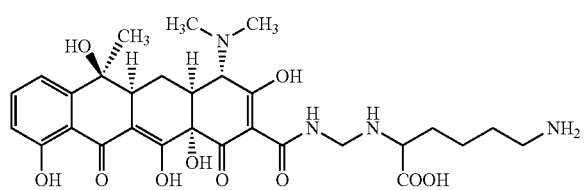

The U.S. Pat. No. 3,042,716 refers that acid addition salts of lymecycline can be formed, namely, the hydrobromic, the phosphoric, the sulfuric, the acetic, the tartaric, the malic, the citric and the gluconic acids but do not refer to the benzoic, succinic, maleic and oxalic acid addition salts. No description on the preparation of these salts is presented and the examples do not teach how to prepare these salts.

In general, the prior art gives insufficient or no detail on the preparation of the organic salts of tetracyclines. Most of the patents disclose the preparation of the salts by stating that they can be prepared by mixing the tetracycline with the organic acid in equimolar proportions or by mixing the tetracycline hydrochloride derivative with a metal salt of the organic acid. When examples are given, the description of the methods is insufficient and no reference is made to technical problems that may be encountered during the preparation of the salts. Moreover, the analytical data presented is insufficient to demonstrate the identity and the purity of the salts. For example, analytical methods showing the formation of the acid addition salt by protonation of the amine groups of the tetracyclines such as $H^1$-NMR, or the presence of the carboxylate anion in the salt, such as the infrared spectra of the product, are not presented. Additionally, the description of salts in the prior art does not provide sufficient analytical data about the purity of the organic acid addition salts obtained. In the course of the work carried out in this invention, technical problems were encountered in the preparation of the organic acid salts of tetracyclines and, contrary to the prior art disclosures, it was observed that, under the conditions described, the products isolated are not the desired salts but the base tetracycline compounds, or, mixtures of the tetracyclines with the organic acids.

Adverse effects of acidic doxycycline inorganic salts are described in the prior art. For example, gastric ulcers induced by doxycycline hydrochloride, a salt with a pH of about 3, have been associated with the caustic effect on the esophageal and gastric mucosa of this very acidic salt. Doxycycline is believed to act through a direct caustic effect on the esophageal and gastric mucosa, likely due to its acidic nature (Reference can be made, for example, to: Gastroenterology Research, 2012, Vol. 5, Nr. 6, December 2012, pages 236-238, Aviva Leber, Jeff Stal, Sherman A, Bini E J. Pill-induced gastric injury. Am J Gastroenterol, 1999; 94(2): 511-513, Carlborg B, Densert O, Lindqvist C.; Laryngoscope, Tetracycline induced esophageal ulcers, a clinical and experimental study 1983; 93(2): 184-187). In animal studies, direct exposure of esophageal mucosa to tetracycline causes deep ulcerations (see, for example: Carlborg B, Densert O, Lindqvist C., Tetracycline induced esophageal ulcers, a clinical and experimental study, Laryngoscope. 1983; 93(2): 184-187). Furthermore the pill formulation is an important contributing factor, with a higher risk of esophageal ulcerations associated with capsules due to their gelatinous shell and tendency to stick and lodge in the esophageal mucosa (see, for example: Corleto Y D, DAlonzo L, Zykaj E, Carnuccio A, Chiesara F, Pagnini C, Di Somma S, et al, A case of oesophageal ulcer developed after taking homeopathic pill in a young woman, World J Gastroenterol. 2007; 13(14):2132-2134].

DESCRIPTION OF THE INVENTION

The present invention relates to new and useful organic salts of tetracyclines which present advantages over salts described in the prior art with respect to adverse effects related to the use of tetracyclines. The salts of tetracyclines of this invention most preferably comprise a tetracycline where the tetracycline is doxycycline, minocycline, sancycline, lymecycline or demeclocycline, and preferably comprise an organic acid where the organic acid can be oxalic acid or maleic acid.

According to one aspect of the present invention, there is provided a tetracycline salt comprising a tetracycline and an organic acid, wherein the organic acid is oxalic acid or maleic acid. The salts are typically acid-addition salts.

In a preferred aspect, the tetracycline is doxycycline, minocycline, sancycline, lymecycline, tetracycline or demeclocycline.

In another preferred aspect, the salt is doxycycline maleate, minocycline oxalate, tetracycline oxalate, demeclocycline maleate, demeclocycline oxalate, sancycline maleate, lymecycline maleate, or lymecycline oxalate.

The invention thus provides, in particular, the following salts as novel salts which have not hitherto been provided:

Doxycycline maleate, Minocycline oxalate, Tetracycline oxalate, Demeclocycline maleate, Demeclocycline oxalate, Sancycline maleate, Lymecycline maleate, and Lymecycline oxalate.

When referring to tetracycline salts of the invention, for example doxycycline maleate, it should be understood that all forms of the salt are to be considered as encompassed by the term. Thus, a reference to "doxycycline maleate" (and this applies equally to all other salts) is to be understood as covering all the different possible forms of the compound—for instance, hydrates, solvates, polymorphs, isomers including stereoisomers, racemic mixtures, and so forth, provided that the tetracycline component and the organic acid component are present in the form of a salt.

According to another aspect of the present invention, there is provided a pharmaceutical formulation comprising a tetracycline salt according to the invention, and one or more pharmaceutically acceptable excipients. Suitably, as will be understood, the formulation will typically comprise one or more pharmaceutically acceptable excipients, according to the nature of the formulation. Any suitable formulation may be used, although preferably, the formulation is an oral, ophthalmic or topical formulation. In one preferred aspect, the formulation is a delayed-release formulation or a sustained release formulation.

The salts and pharmaceutical formulations of the invention preferably have a higher pH than the equivalent formulation based upon the hydrochloride salt of the tetracycline. Preferably, the salts and formulations are characterized by a pH in aqueous solution of equal to, or higher than, 3. In particular the invention provides a salt according to the invention characterized by a pH in aqueous solution of equal to, or higher than, 3.

In another aspect, the salts or pharmaceutical formulations of the invention are also characterized by being slightly bitter or tasteless in aqueous solution on the bitter taste standard scale based on quinine hydrochloride.

There is also provided a salt, or corresponding pharmaceutical formulation, according to the invention characterized by having a lower solubility in aqueous solution than the corresponding hydrochloride salt or hyclate salt. Doxycycline oxalate and doxycycline maleate are particular examples of this, particularly when compared to doxycycline hydrochloride.

There is also provided a salt, or corresponding pharmaceutical formulation, according to the invention characterized by having a lighter color according to the Munsell classification than a corresponding inorganic salt, in particular the corresponding hydrochloride salt or hyclate salt. Again, doxycycline oxalate and doxycycline maleate are particular examples of this, particularly when compared to the corresponding hyclate salt.

In a further aspect, the invention also provides a medical device having coated thereon a salt or a formulation according to the invention. Any suitable device may be used, but preferably the medical device is an implant. For example, the implant may be a catheter and/or a stent.

In a further aspect, the invention also provides a salt of the invention, or a formulation of the invention, for use as a medicament, particularly in the treatment or prevention of an inflammation and/or an infection. Any such condition may be treated, but the invention is particularly useful wherein the infection and/or inflammation are an infection or inflammation of the eye. The salt or formulation may, for example, be coated onto a medical device, such as an implant, for example a catheter and/or a stent.

In another aspect, this invention is related to a method of preparing organic salts of tetracyclines, said method comprising the dissolution of the tetracycline in the basic form in a solvent containing an excess of an organic acid. The organic salt of the tetracycline precipitates out of the reaction mixture. The product may then be filtered, and typically is washed with the solvent used in the reaction, and afterwards is dried. Conventional methods for these steps may be used.

Thus, the invention also provides a method of preparing a tetracycline salt, which method comprises reacting a tetracycline base with an excess of an organic acid in a solvent.

The tetracycline used in the salt preparation is suitably doxycycline, minocycline, sancycline, lymecycline, tetracycline or demeclocycline. Preferred salts which can be prepared according to the method of the invention include doxycycline maleate, minocycline oxalate, tetracycline oxalate, demeclocycline maleate, demeclocycline oxalate, sancycline maleate, lymecycline maleate, or lymecycline oxalate.

The organic acid used in the method is most preferably oxalic acid or maleic acid. Preferably, the excess of the organic acid is more than one molar equivalent with respect to the tetracycline. The excess of the organic acid may be 5 or more molar equivalents with respect to the tetracycline.

Any suitable solvent may be used, and suitable solvents for use with tetracyclines will be known to those skilled in this field. The solvent is typically an organic solvent and may, for example, be an alcohol or a mixture of an alcohol with an amide solvent, such as dimethylformamide, although it will be understood other suitable amide solvents may be used. Preferably, the solvent is an alcohol. More preferably, the solvent is methanol or a mixture of methanol and dimethylformamide. The organic acid is suitably used in an amount higher than one molar equivalent with respect to the tetracycline. Preferably, it is used in an amount of 5 molar equivalents or more with respect to the tetracycline.

For example, the preparation of doxycycline maleate and doxycycline oxalate can be carried out by reaction of the doxycycline base with the corresponding acid. Preferably, the reaction is carried out in an alcohol.

The present invention thus relates to new and useful organic salts of tetracyclines which present advantages over salts described in the prior art regarding adverse effects related to the use of tetracyclines. More particularly, it is concerned with liposoluble tetracycline salts which exhibit adequate pH values for preventing irritating effects, such as gastric and ophthalmic injuries, induced by administration of more acidic forms of tetracyclines. Another important technical feature of the salts of this invention is their low water solubility and this presents an advantage for delayed-release and sustained-released formulations. One further advantage of the salts of this invention is their lower luminosity when compared with the luminosity (lighter color) of the prior art salts, an advantageous technical feature for hyper-pigmentation adverse effects induced by long term therapy of tetracyclines. Additionally, the salts herein disclosed present a less intense bitter taste, an advantageous technical feature for oral administration medicines. The present invention also relates to an improved method for preparing tetracycline organic salts.

In attempts to prepare the organic salts acetate, succinate, maleate and oxalate of doxycycline by reaction of doxycycline hydrochloride derivative with the corresponding basic metal salt of the organic acid in aqueous medium it was observed that precipitation of doxycycline base occurred from the reaction mixture instead of precipitation of the respective organic salt. These examples illustrate a technical difficulty encountered when following the prior art disclosures.

Another technical difficulty is that the isolated tetracycline organic salt may retain unreacted tetracycline base and is not a pure tetracycline organic salt. The present inventors found that, surprisingly, an excess of organic acid was required to promote complete dissolution of the tetracycline prior to the start of the crystallization of the organic salt of the tetracycline. Complete dissolution of the tetracycline base is required to ensure complete consumption of this starting material. This is an important technical feature of the method herein disclosed because, if the tetracycline does not dissolve completely, the tetracycline organic salt which crystallizes out of the reaction mixture is not pure and contains residual amounts of the tetracycline base.

Certain salts of this invention exhibit a less acidic pH than the corresponding hydrochloride salt and their administration will avoid or minimise the development of gastrointestinal injuries related to the acidic nature of the salt. The pH of the maleate and oxalate salts of doxcycline is less acidic than that of the hyclate salt as disclosed in the table below. The pH of the oxalate salt of tetracycline is less acidic than the pH of tetracycline. Hence, the risk of inducing gastric injuries when using these salts is reduced when compared with that of the acidic hydrochlorides.

|  | pH |
|---|---|
| Doxycycline | |
| Doxycyline Maleate | 3.3 |
| Doxycyline Oxalate | 3.2 |
| Doxycyline Hyclate | 2.0 to 3.0 |
| Doxycyline Monohydrate | 5.0 to 6.5 |
| Demeclocycline | |
| Demeclocycline Maleate | 3.4 |
| Demeclocycline Oxalate | 3.3 |
| Minocycline | |
| Minocycline Oxalate | 3.0 |
| Minocycline Hydrochloride | 3.5 to 4.5 |
| Minocycline Base | 6.8 |
| Tetracycline | |
| Tetracycline Oxalate | 3.2 |
| Tetracycline hydrochloride | 1.8 to 2.8 |

The pH data presented above for the organic acids salts was measured in aqueous solutions of the products with a concentration of approximately $10^{-3}$ M and the pH ranges for the products available on the market are those disclosed in European and US pharmacopoeia monographs.

The moderate acidic behavior can be beneficial for administration of drugs to treat eye infections or eye inflammations because of the risks associated to chemical eye injury. Chemical eye injury is an ophthalmic emergency, which may be caused by exposure to an acidic (pH<4) or an alkali (pH>10) solution to the eye (see, for example: Int J Ophthalmol. 2014; 7(6): 1067-1068). To manage the adverse effects of chemical eye injury, copious irrigation with clean or sterile water or Ringer's solution (pH 7.3-7.4) or its equivalent, of a near neutral pH is required. Irrigating volumes of up to 20 litres or more are sometimes required to achieve physiological pH level. However, patients may feel intense pain after initial irrigation caused by both epithelial defect and ciliary body irritation. On many occasions local anesthetic eye drops are used to reduce eye pain, which can help in better eye opening for detailed examination.

In one aspect, the use of the salts of this invention in oral formulations present the advantage over the prior art salts of not promoting adverse effects related to the acidic nature of the active pharmaceutical substance. In another aspect, the salts of this invention present the advantage over the prior art salts of not promoting adverse effects related to the basic nature of the active pharmaceutical substance. In yet another aspect, the salts of this invention can be used for new applications where irritation of soft tissues, for example, the mucosa, needs to be prevented, such as nasal applications, inhalation applications, ophthalmic applications, oral applications or dental applications.

The solubility of the salts of this invention was measured at pH=1.0, pH=1.2, pH=4.5, pH=6.8 and pH=7.5, respectively and the results are presented in the next table. The buffers at pH 1.0 and 1.2 were prepared with aqueous solutions of potassium chloride 0.2M and hydrochloric acid 0.2 M, the buffers at pH 6.8 and 7.5 were prepared with aqueous solutions of monobasic potassium phosphate 0.2 M and sodium hydroxide 0.2 M and the buffer at pH 4.5 with aqueous solutions of potassium biphthalate 0.2 M and hydrochloric acid 0.2 M, according to pharmacopoeia USP31.

| | Solubility | | | | |
|---|---|---|---|---|---|
| "Tetracyclines" | pH = 1.0 | pH = 1.2 | pH = 4.5 | pH = 6.8 | pH = 7.5 |
| Doxycyline Maleate | Soluble 13 ml/g | Soluble 13 ml/g | Sparingly Soluble 63 ml/g | Sparingly Soluble 83 ml/g | Sparingly Soluble 77 ml/g |
| Doxycyline Oxalate | Slightly Soluble 500 ml/g | Very Slightly Soluble 1900 ml/g | Slightly Soluble 500 ml/g | Slightly Soluble 125 ml/g | Slightly Soluble 143 ml/g |
| Doxycyline Hyclate | Soluble 16 ml/g | Freely soluble 3 ml/g | Sparingly Soluble 53 ml/g | Freely soluble 2 ml/g | Sparingly Soluble 100 ml/g |
| Doxycyline Monohydrate | Soluble 19 ml/g | Soluble 25 ml/g | Slightly Soluble 1000 ml/g | Slightly Soluble 333 ml/g | Slightly Soluble 1000 ml/g |
| Demeclocycline Maleate | Soluble 30 ml/g | Soluble 30 ml/g | Sparingly Soluble 38 ml/g | Sparingly Soluble 77 ml/g | Sparingly Soluble 67 ml/g |
| Demeclocycline Oxalate | Freely soluble 10 ml/g | Soluble 18 ml/g | Sparingly Soluble 53 ml/g | Sparingly Soluble 34 ml/g | Sparingly Soluble 77 ml/g |
| Minocycline Oxalate | Soluble 1 ml/g | Soluble 1 ml/g | Freely soluble 10 ml/g | Soluble 5 ml/g | Freely soluble 8 ml/g |
| Minocycline Hydrochloride | Soluble 25 ml/g | Soluble 3 ml/g | Sparingly Soluble 38 ml/g | Sparingly Soluble 37 ml/g | Sparingly Soluble 36 ml/g |
| Minocycline Base | Soluble 14 ml/g | Soluble 20 ml/mg | Soluble 19 ml/g | Slightly Soluble 200 ml/g | Slightly Soluble 111 ml/g |
| Tetracycline | Soluble 25 ml/g | Sparingly Soluble 50 ml/g | Slightly Soluble 200 ml/g | Slightly Soluble 250 ml/g | Slightly Soluble 333 ml/g |
| Tetracycline Oxalate | Sparingly Soluble 50 ml/g | Soluble 17 ml/g | Sparingly Soluble 77 ml/g | Sparingly Soluble 83 ml/g | Slightly Soluble 167 ml/g |

A distinct feature of the salts of this invention is that their solubility profile is distinct from that of the corresponding hydrochloride salts as well as that of the base compounds. At pH=1.0, pH=1.2, pH=4.5, pH=6.8 and pH=7.5 the solubility of doxycycline maleate is similar to that of the hydrochloride but at pH=1.0 and pH=1.2 is similar to that of doxycycline monohydrate whilst at pH=4.5, pH=6.8 and pH=7.5 is higher than that of the monohydrate. On the other hand, the solubility of doxycycline oxalate is lower than that of the hyclate at all pH values tested whilst it is lower than that of the monohydrate at pH=1.0 and pH=1.2 and it is similar at pH=4.5, pH=6.8 and pH=7.5.

Surprisingly, the oxalate salt of minocycline is more soluble than the corresponding hydrochloride and base compounds at all pH values tested. Moreover, minocycline oxalate is much more soluble than any of the other tetracycline compounds listed in the solubility table.

The statement freely soluble means that the volume of solvent (required for dissolution) in ml per gram of solute is of from 1 to 10. The statement soluble means that the volume of solvent (required for dissolution) in ml per gram of solute is of from 1 to 30. The statement sparingly soluble means that the volume of solvent (required for dissolution) in ml per gram of solute is of from 30 to 100. The statement slightly soluble means that the volume of solvent (required for dissolution) in ml per gram of solute is of from 100 to 1000. The statement very slightly soluble means that the volume of solvent (required for dissolution) in ml per gram of solute is from 1000 to 10 000.

The low solubility of the salts of this invention is an advantage for delayed release and/or sustained release medicines. Delayed-release or sustained-release formulations are used to promote slow dissolution and slow release of a drug over time. The advantage of these medicines relies on the fact that they can be taken less frequently than instant-release preparations thus maintaining steady levels of the drug in the blood stream. Usually, these medicines use insoluble substances where the active pharmaceutical substance may be embedded and afterwards released in the active site through holes of a matrix or through porous of a membrane. The use of liposoluble active pharmaceutical ingredients in these formulations reinforces the delay of the release of the drug in the active site. In another aspect, therefore, the use of the salts of this invention in delayed release and sustained release formulations presents the advantage over the prior art salts of improving the delayed or sustained release profile of the active pharmaceutical substance.

Sustained release formulations are particularly useful in medical devices coated with active pharmaceutical ingredients. The particles of the active pharmaceutical ingredients are disposed on a device surface and effectively adhere to its surface thus allowing a controlled release of the active pharmaceutical ingredient from the device surface to a desired treatment. The medical device is suitable for insertion or implantation into a subject. API coated medical devices are used to treat or prevent diseases in humans, more specifically, have been used for the localized delivery of active pharmaceutical ingredients. The active pharmaceutical ingredients used have one or more therapeutic activities such as antibacterial activity, anti-inflammatory activity, antiproliferative activity, vasodilatory activity, or lipid-lowering activity. The use of coated medical devices in the treatment of cardiovascular diseases is well known. In another aspect, the salts of this invention present an advantage over the prior art salts regarding their low solubility in water aqueous media and consequent slow dissolution thus making them preferred for slow delayed release and sustained release formulations coated on the surface of medical devices.

The salts of this invention exhibit a lighter color than the color of the inorganic salts of doxycycline. The color of doxycycline hyclate according to the Munsell color system is yellowish 10Y whilst the organic salts herein described are off-white to yellowish 5Y which means a lower luminosity. The table below presents the color classification of the doxycycline salts according to the Munsell color system.

| "Tetracycline" | Color Description | Munsell Classification |
|---|---|---|
| Doxycycline Hyclate | Yellowish | 10Y 9/3.5 NN |
| Doxycycline Monohydrate | Yellowish | 10Y/9/3.5 NN |
| Doxycycline Oxalate | Yellowish | 5Y/9/4 NN |
| Doxycycline Maleate | Off-white | 9.25/10Y/2.5 NN |
| Minocycline Base | Yellowish | 7.5Y/9/10 NN |
| Minocycline Oxalate | Yellowish | 10/Y/9/3.5 NN |
| Demeclocycline Maleate | Yellowish | 5Y/9/2 NN |
| Demeclocycline Oxalate | Yellowish | 5Y/9/2.5 NN |
| Tetracycline base | Yellowish | 5Y/9/4 NN |
| Tetracycline Oxalate | Yellowish | 10Y/9/8 NN |

Lower luminosity can be an advantage for hyperpigmentation adverse effects induced by tetracyclines upon long term use of tetracyclines. The hyperpigmentation adverse effects have been observed on the skin, on mucosal surfaces, on the teeth on the nails and also on the eyes. Children can develop permanent brown discoloration of the teeth due to drug deposition, probably due to the chelating properties of tetracyclines and the formation of a tetracycline-calcium orthophosphate complex. Based on this rationale, it is not recommended to administer tetracyclines to pregnant women after the fourth month of pregnancy and to children after birth and until eight years of age. Other mechanisms have been proposed for the hyperpigmentation adverse effects. One of the mechanisms proposed for the tetracyclines induced discoloration is the accumulation of the drug under any layer of the skin, usually the dermis or epidermis. The accumulation of tetracyclines exhibiting a lower luminosity, particularly the ones exhibiting off-white color, will not induce discoloration.

In another aspect, some of the salts of this invention present a less intense bitter taste than that of quinine hydrochloride, the bitter taste standard. When compared to the active substances in the market, a few of the salts present a more pleasant taste.

| Tetracycline | Taste |
|---|---|
| Quinine hydrochloride | Bitter |
| Doxycycline Hyclate | Slightly bitter |
| Doxycycline Monohydrate | Slightly bitter, almost tasteless |
| Doxycycline Oxalate | Slightly bitter |
| Doxycycline Maleate | Slightly bitter, fruit like |
| Minocycline hydrochloride | Almost tasteless |
| Minocycline Base | Almost tasteless, acidic |
| Minocycline Oxalate | Slightly bitter, citrine like |
| Demeclocycline Maleate | Unpleaseant, oil like |
| Demeclocycline Oxalate | Bitter, acidic |
| Tetracycline base | Almost tasteless |
| Tetracycline Oxalate | Almost tasteless, acidic |

The taste comparison was performed with aqueous solutions with a concentration of 0.5 mg/ml of each one of the compounds tested.

Taste is an important technical feature of oral administration medicines. Many active pharmaceutical substances taste bitter and are aversive to children as well as many adults thus creating problems of adherence to the therapy (i.e. patient compliance). More than 90% of pediatricians reported that a drug's taste and palatability were the biggest barriers to completing treatment (see, for example: Milne C P, Bruss J B. The economics of pediatric formulation development for off-patent drugs. Clin. Ther. 2008; 30(11):2133-2145.

Encapsulation of the medicine in pill or tablet form, or addition of taste-masking ingredients such as sugars or pleasant flavorings may help avoid the unpleasant taste however, some of these ingredients cannot be added to solid dose forms and, additionally, they often are not effective in suppressing bitter tastes. The use of active pharmaceutical ingredients exhibiting a less intense bitter taste will improve the taste of solid dosages formulation thus contributing to better adherence to the therapy.

EXAMPLES

The examples below are illustrative and are not intended in any way to limit the scope of the invention.

Example 1 (Doxycycline Oxalate)

To a solution of oxalic acid (10.80 g) in methanol (80 ml), previously cooled to a temperature between 5° C. and 0° C. and under inert atmosphere, was added doxycycline monohydrate (10 g) whilst maintaining the temperature between 0° C. and 5° C. The mixture stirred over 1 hour at 0° C./5° C., under inert atmosphere. The suspension was filtered and the wet product was washed with methanol (80 ml) previously cooled to 5° C./0° C. The wet product was dried under reduced pressure at room temperature. Doxycycline oxalate was obtained (5.94 g), 99.65% pure by HPLC area %. The IR spectrum in KBr presented the carboxylate group $COO^-$ bands, one between 1586 $cm^{-1}$ and 1618 $cm^{-1}$, and the other at 1339 $cm^{-1}$. The NMR spectrum in deuterated DMSO presented the N-Me protons as a singlet at 2.67 ppm, showing a shift to a lower field, when compared with the starting material. The melting point by DSC was 147.0° C. The XRPD diffractogram presents peaks at 2 theta degrees (+/−0.2 degrees theta) 6.04, 10.16, 11.90, 16.40, 17.80, 19.24 and 20.04.

Example 2 (Doxycycline Maleate)

To methanol (80 ml) it was added maleic acid (14.02 g) and the solution was cooled to 5° C./0° C., under inert atmosphere. Doxycycline monohydrate (10 g) was added while maintaining the mixture at 5° C./0° C. and inert atmosphere. Methyl tert-butyl ether (960 ml) was added to the mixture and the resulting suspension stirred for 1 h at 5° C./0° C. The product was filtered, was washed with a mixture of methyl tert-butyl ether (74 ml) and methanol (6 ml) previously cooled to 5° C./0° C. and after was dried under reduced pressure at 40° C. The product was obtained 99.08% pure by HPLC area % (9.48 g), and was doxycycline maleate with a melting point of 137.0° C. The IR spectrum in KBr presented the two bands of the $COO^-$ group, at 1617 $cm^{-1}$ and 1363 $cm^{-1}$. The NMR spectrum in deuterated DMSO presented the N-Me protons as a singlet at 2.73 ppm, showing a shift to a lower field, when compared with the starling material. The XRPD diffractogram presents no peaks and corresponds to an amorphous solid.

Example 3: (Minocycline Oxalate)

Oxalic acid (1.52 g) was added to methanol (16 ml) and the resulting solution was cooled to a temperature between −10° C. and 0° C., under inert atmosphere. Minocycline base (1 g) was added while keeping the temperature between −10° C. and 0° C. The mixture stirred over 1 hour at −10° C./0° C., under inert atmosphere. The product precipitated by adding of diethyl ether (50 ml) at room temperature. The suspension was filtered, the wet product was washed with diethyl ether (80 ml) at room temperature and was dried under vacuum. Minocycline oxalate (0.83 g) was obtained. The IR spectrum in KBr presented the two characteristic bands of the carboxylate group $COO^-$ in resonance, one at 1618 $cm^{-1}$ and the other at 1403 $cm^{-1}$. The XRPD diffractogram showed that the sample was amorphous. The NMR spectrum in deuterated DMSO presented the N-Me protons as two singlets: one at 2.54 ppm, and another one at 2.69 ppm, showing a shift to a lower field, when compared with the starting material.

Example 4 (Tetracycline Oxalate)

Oxalic acid (3.02 g) was added to methanol (16 ml) and the resulting solution was cooled to a temperature between −10° C. and 0° C., under inert atmosphere. Tetracycline monohydrate (2 g) was added while keeping the temperature between −10° C. and 0° C. The mixture stirred over 1 hour at −10° C./0° C., under inert atmosphere. The product (tetracycline oxalate) precipitated by addition of diethyl ether (100 ml). The suspension was filtered, the wet product was washed with diethyl ether (80 ml) and was dried under vacuum. The IR spectrum in KBr presented the two characteristic bands of the carboxylate group $COO^-$ in resonance, one at 1615 $cm^{-1}$ and the other at 1403 $cm^{-1}$. The XRPD difractogram showed that the sample was amorphous. The NMR spectrum in deuterated DMSO presented the N-Me protons as two singlets: one at 2.62 ppm and another at 2.90 ppm, showing a shift to a lower field, when compared with the starting material.

Example 5 (Demeclocycline Maleate)

Maleic acid (12.48 g) was added to diethyl ether (400 mL) and the resulting solution was stirred at room temperature. Demeclocycline monohydrate (10 g) was added to methanol (400 mL) and then added dropwise to the maleic acid solution. The mixture stirred over 1 hour at 0° C./5° C. The suspension was filtered, the wet product was washed with water (100 ml) previously cooled to 5° C./0° C. and was dried under reduced pressure at room temperature. Demeclocycline maleate was obtained. The IR spectrum in KBr presented one of the two characteristic bands of the carboxyiate group $COO^-$ in resonance, one at 1578 $cm^{-1}$ and the other at 1340 $cm^{-1}$. The $COO^-$ symmetrical vibration wasn't assigned due to the complexity of the fingerprint zone. The XRPD diffractogram presents peaks at 2 theta degrees (+/−0.2 degrees theta) 6.82, 8.32, 11.02, 12.46, 13.38, 15.5, 17.06, 17.62, 20.64, 21.14, 22.92. The NMR spectrum in deuterated DMSO presented the N-Me protons as a singlet at 2.74 ppm (showing a shift to a lower field, when compared with the starting material). The vinyl protons of the maleate were identified by a singlet at 6.09 ppm.

Example 6 (Demeclocycline Oxalate)

Oxalic acid (15 g) was added to methanol (160 ml) and the resulting solution was cooled to a temperature between −10° C. and 0° C., under inert atmosphere. Demeclocycline monohydrate (10 g) was added while keeping the temperature between −10° C. and 0° C. The mixture stirred over 1 hour at −20° C./0° C., under inert atmosphere. The suspension was filtered, the wet product was washed with diethyl ether (80 ml) previously cooled to −10° C./0° C. and was dried under reduced pressure at room temperature. Demeclocycline oxalate was obtained. The IR spectrum in KBR presented the two characteristic bands of the carboxylate group COO⁻ in resonance, one at 1615 $cm^{-1}$ and the other at 1403 $cm^{-1}$. The XRPD diffractogram presents peaks at 2theta degrees (+/−0.2 degrees theta) 8.62, 10.24, 10.92, 12.06, 13.28, 14.96, 16.20, 17.64, 18.86, 19.18, 20.96, 21.66, 21.86, 22.36, 23.12, 24.70, 26.16, 26.60, 26.76. The NMR spectrum presented the N-Me protons as one singlet at 2.59 ppm (showing a shift to a lower field, when compared with the starting material).

Infrared Spectra (IR) spectra were collected from a Perkin-Elmer Spectrum 1000, in KBr pellets.

Nuclear Magnetic Resonance (NMR) measurements were made using Bruker, Avance III 400, probe QNP Z-GRD Z8400-0250 of 5 mm, peak reference $Si(CH_3)_3$, scanning range 0-10 ppm, samples dissolved in deuterated dimethylsulfoxide (DMSO).

Differential Scanning Calorimetry (DSC) measurements were made using TA Instruments, DSC Q2000 Y24.9 Build 121, Sample weight 4-10 mg), Heating rate: 5° C./min, Scan range: 30-250° C., in $N_2$ stream, flow rate 40 ml/min.

X-Ray Powder Diffraction (XRPD) measurements were made using RIGAKU MiniFlex II, X-ray source of CuKα (30 KV/15 mA), scanning range 0°-50° 2□, continuous scan, rate: 3°/min, accuracy of peak positions+/−0.2°

The invention claimed is:

1. A tetracycline salt comprising a tetracycline and an organic acid, wherein the organic acid is oxalic acid or maleic acid and the tetracycline is doxycycline, minocycline, sancycline, lymecycline, or demeclocycline.

2. The salt according to claim 1 wherein the salt is doxycycline maleate, minocycline oxalate, demeclocycline maleate, demeclocycline oxalate, sancycline maleate, lymecycline maleate, or lymecycline oxalate.

3. The salt according to claim 1 characterized by a pH in aqueous solution of equal to, or higher than, 3.

4. The salt according to claim 1 characterized by being slightly bitter or tasteless in aqueous solution on the bitter taste standard scale based on quinine hydrochloride.

5. The salt according to claim 1 characterized by having a lower solubility in aqueous solution than the corresponding hydrochloride salt or hyclate salt.

6. The salt according to claim 1 characterized by having a lighter color according to the Munsell classification than a corresponding inorganic salt, in particular the corresponding hydrochloride salt or hyclate salt.

7. A pharmaceutical formulation comprising the tetracycline salt according to claim 1 and one or more pharmaceutically acceptable excipients.

8. The pharmaceutical formulation according to claim 7 wherein the formulation is an oral, ophthalmic or topical formulation.

9. The pharmaceutical formulation according to claim 7 wherein the formulation is a delayed-release formulation or a sustained release formulation.

10. A medical device having coated thereon a salt according to claim 1, or a pharmaceutical formulation comprising the tetracycline salt according to claim 1 and one or more pharmaceutically acceptable excipients.

11. The medical device according to claim 10 wherein the medical device is an implant.

12. The medical device according to claim 11 wherein the implant is a catheter and/or a stent.

13. A method comprising utilizing the salt according to claim 1, or a pharmaceutical formulation comprising the tetracycline salt according to claim 1 and one or more pharmaceutically acceptable excipients as a medicament.

14. A method of treatment comprising inserting or implanting the medical device of claim 10 into a subject in need thereof.

15. A method of treatment comprising inserting or implanting the medical device of claim 11 into a subject in need thereof.

16. A method of treatment comprising inserting or implanting the medical device of claim 12 into a subject in need thereof.

17. A method of preparing a tetracycline salt, which method comprises reacting a tetracycline base with an excess of an organic acid in a solvent, wherein the tetracycline salt is according to claim 1.

18. The method according to claim 17 wherein the organic acid is oxalic acid or maleic acid.

19. The method according to claim 17 wherein the excess of the organic acid is more than one molar equivalent with respect to the tetracycline.

20. The method according to claim 19 wherein the excess of the organic acid is 5 or more molar equivalents with respect to the tetracycline.

21. The method according to claim 17 wherein the solvent is an alcohol or a mixture of an alcohol with an amide solvent.

22. The method according to claim 17 wherein the solvent is methanol or a mixture of methanol and dimethylformamide.

23. The method according to claim 17 wherein the tetracycline base is completely dissolved in the solvent prior to crystallisation of the salt.

\* \* \* \* \*